US012618829B2

(12) United States Patent
Ichihashi et al.

(10) Patent No.: US 12,618,829 B2
(45) Date of Patent: May 5, 2026

(54) METHOD OF ANALYZING NEURONS, DEVICE FOR ANALYZING NEURONS, AND COMPUTER PROGRAM

(71) Applicant: NIKON CORPORATION, Tokyo (JP)

(72) Inventors: Toru Ichihashi, Yokohama (JP); Takahiko Yoshida, Tokyo (JP); Moeka Nobuta, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 358 days.

(21) Appl. No.: 18/220,571

(22) Filed: Jul. 11, 2023

(65) Prior Publication Data

US 2023/0408494 A1      Dec. 21, 2023

Related U.S. Application Data

(63) Continuation of application No. PCT/JP2022/001618, filed on Jan. 18, 2022.

(30) Foreign Application Priority Data

Jan. 26, 2021      (JP) ................................. 2021-010409

(51) Int. Cl.
*G01N 33/50*          (2006.01)
*C12M 1/34*          (2006.01)
(52) U.S. Cl.
CPC ......... *G01N 33/5058* (2013.01); *C12M 41/46* (2013.01)
(58) Field of Classification Search
None
See application file for complete search history.

(56) References Cited

U.S. PATENT DOCUMENTS 6,514,722 B2 *    2/2003    Palsson .............. G01N 33/5091
                                                                        435/7.1
2008/0176276 A1    7/2008    Arai
                            (Continued)

FOREIGN PATENT DOCUMENTS

JP          2006-314214 A      11/2006
JP          2009-072155 A      4/2009
                            (Continued)

OTHER PUBLICATIONS

Jun. 25, 2024 Office Action issued in Japanese Patent Application No. 2022-578267.
                            (Continued)

*Primary Examiner* — Darryl V Dottin
(74) *Attorney, Agent, or Firm* — Oliff PLC

(57)                ABSTRACT

A method of analyzing neurons includes: identifying a cell region by identifying a region of a neurite or a region of a cell body of a neuron on the basis of time-series images obtained by imaging the neuron in time series; detecting aggregates by imaging, in time series, first fluorescent protein tagged to specific protein expressed in the neuron and detecting presence or absence of aggregates of the specific protein aggregated in the region of the neurite or the region of the cell body identified in the identifying the cell region on the basis of luminance of the first fluorescent protein included in the time-series images; and performing an analysis by classifying the neuron into a plurality of groups on the basis of a detection result of the detecting the aggregates and analyzing a survival state of the neuron for each of the groups.

15 Claims, 23 Drawing Sheets

(56) References Cited

U.S. PATENT DOCUMENTS

| | | | | |
|---|---|---|---|---|
| 2011/0076235 A1* | 3/2011 | Tully | ................. | G01N 33/5058 |
| | | | | 424/9.2 |
| 2015/0038338 A1* | 2/2015 | Rinberg | ............. | G01N 33/5058 |
| | | | | 506/9 |
| 2018/0314876 A1 | 11/2018 | Rubin et al. | | |
| 2020/0043159 A1 | 2/2020 | Watanabe et al. | | |
| 2021/0024621 A1 | 1/2021 | Urushitani et al. | | |

FOREIGN PATENT DOCUMENTS

| | | | |
|---|---|---|---|
| JP | 2012-163538 | A | 8/2012 |
| JP | 2014-085949 | A | 5/2014 |
| JP | 2014-103900 | A | 6/2014 |
| JP | 2018-518154 | A | 7/2018 |
| WO | 2018/066039 | A1 | 4/2018 |
| WO | 2019/177138 | A1 | 9/2019 |

OTHER PUBLICATIONS

Mar. 29, 2022 International Search Report issued in International Patent Application No. PCT/JP2022/001618.
Mar. 29, 2022 Written Opinion issued in International Patent Application No. PCT/JP2022/001618.

* cited by examiner

S200

FROM START

ACQUIRE DATA OF BIRD-VIEW IMAGE OF NEURON
AND DISPLAY DATA ON OUTPUT UNIT — S201

NO    INPUT
CONDITION FOR TIME-LAPSE
IMAGING? — S202

YES

GENERATE RECIPE FOR TIME-LAPSE IMAGING
ACCORDING TO INPUT CONDITION — S203

NO    INSTRUCT TO START
TIME-LAPSE IMAGING? — S204

YES

START TIME-LAPSE IMAGING — S205

NO    END TIME-LAPSE IMAGING? — S206

YES

TO S210

211a

212a 212a                 213a

213a    214a

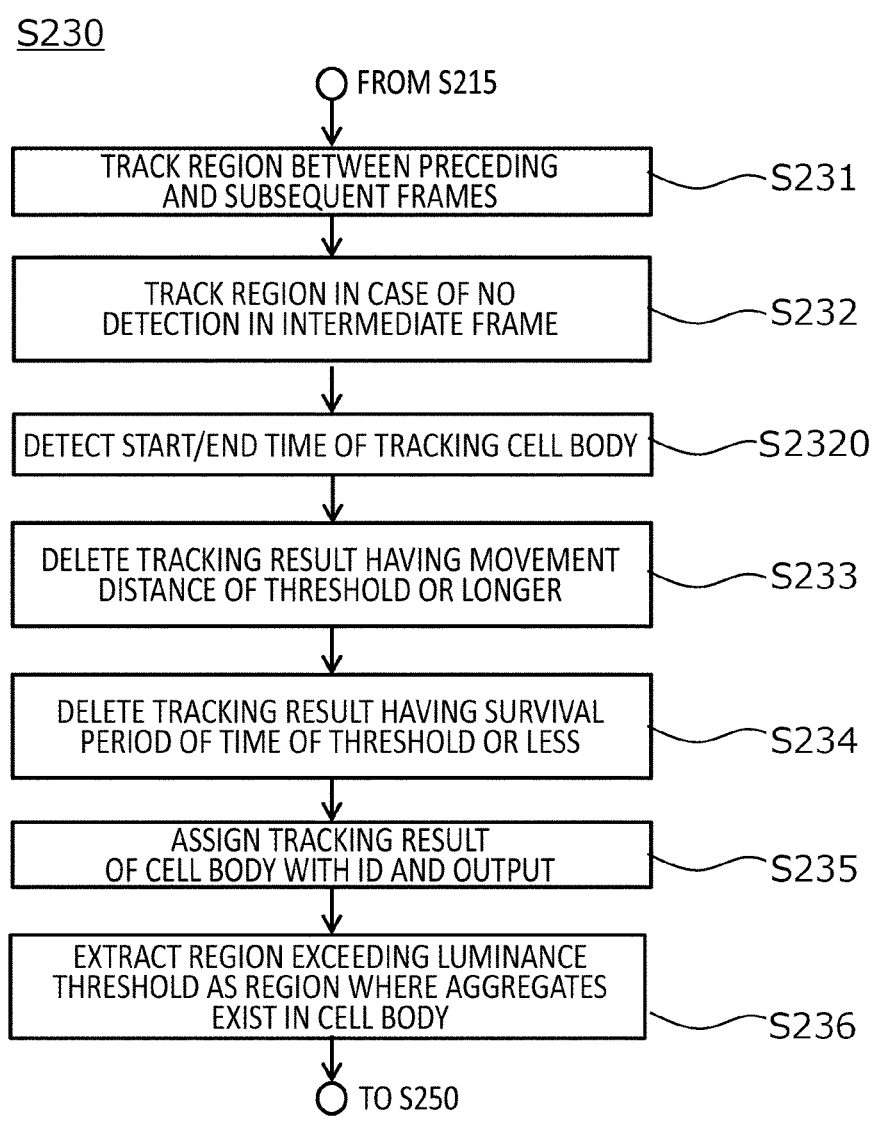

S230

FROM S215

TRACK REGION BETWEEN PRECEDING AND SUBSEQUENT FRAMES — S231

TRACK REGION IN CASE OF NO DETECTION IN INTERMEDIATE FRAME — S232

DETECT START/END TIME OF TRACKING CELL BODY — S2320

DELETE TRACKING RESULT HAVING MOVEMENT DISTANCE OF THRESHOLD OR LONGER — S233

DELETE TRACKING RESULT HAVING SURVIVAL PERIOD OF TIME OF THRESHOLD OR LESS — S234

ASSIGN TRACKING RESULT OF CELL BODY WITH ID AND OUTPUT — S235

EXTRACT REGION EXCEEDING LUMINANCE THRESHOLD AS REGION WHERE AGGREGATES EXIST IN CELL BODY — S236

METHOD OF ANALYZING NEURONS, DEVICE FOR ANALYZING NEURONS, AND COMPUTER PROGRAM

This application is a continuation application, filed under 35 U.S.C. § 111(a) of International Patent Application No. PCT/JP2022/001618 filed on Jan. 18, 2022, which claims priority benefit from Japanese Patent Application No. 2021-010409 filed on Jan. 26, 2021, the contents of each of which are incorporated herein by reference in their entireties.

BACKGROUND

1. Technical Field

The present invention relates to a method of analyzing neurons, a device for analyzing neurons, and a computer program.

2. Related Art

Fluorescence observation of cells has been performed by introducing a gene encoding fluorescent protein into a living cell. As the fluorescent protein, green fluorescent protein (GFP), red fluorescent protein (RFP), and the like are used. These types of fluorescent protein are used as markers indicating localization of genes in cells and protein in cells.

Patent Document 1 describes a method of introducing a gene encoding fluorescent protein into a plurality of cells and synchronizing cell cycles by using, as an index, fluorescence emitted from the cells. There is a need for a new technique for analyzing cells by using the fluorescent protein.

Patent Document 1: Japanese Patent Application Publication No. 2009-072155

GENERAL DISCLOSURE

In a first aspect of the present invention, a method of analyzing neurons is provided. The method of analyzing neurons may include acquiring an image by acquiring time-series images obtained by imaging a neuron in time series. The method of analyzing neurons may include identifying a cell region by identifying a region of a neurite or a region of a cell body of the neuron on the basis of the time-series images. The method of analyzing neurons may include detecting aggregates by detecting, on the basis of the time-series images obtained by imaging, in time series, first fluorescent protein tagged to specific protein expressed in the neuron, presence or absence of aggregates of the specific protein aggregated in the region of the neurite or the region of the cell body identified in the identifying the cell region by using, as a basis, luminance of the first fluorescent protein included in the time-series images. The method of analyzing neurons may include performing an analysis by classifying the neuron into a plurality of groups on the basis of a detection result of the detecting the aggregates and analyzing a survival state of the neuron for each of the groups. The performing the analysis may include displaying, for each of the groups, a relationship between the plurality of groups and survival states of the plurality of groups.

In a second aspect of the present invention, the time-series images may have at least one of data of a phase difference image, data of a fluorescence image including the luminance of the first fluorescent protein, or data including a moving image file.

In a third aspect of the present invention, the identifying the cell region may include imaging, in time series, the first fluorescent protein tagged to the specific protein expressed in the neuron in the acquiring the image. The identifying the cell region may include identifying, as the region of the neurite of the neuron, a region where the luminance of the first fluorescent protein in the time-series images exceeds a first luminance threshold.

In a fourth aspect of the present invention, the identifying the cell region may include identifying, as the region of the neurite or the cell body of the neuron, a region exceeding a predetermined size threshold among regions including the region where the luminance of the first fluorescent protein in the time-series images exceeds the first luminance threshold. In the identifying the cell region, each of the neurite being identified and identical and the cell body being identified and identical may be tracked in time series, and a survival period of time related to the survival state may be calculated.

In a fifth aspect of the present invention, the detecting the aggregates may include detecting the region of the neurite identified in the identifying the cell region as a region where the aggregates of the specific protein exist. The detecting the aggregates may include recognizing, as one aggregate region, a plurality of the aggregates in which a distance between regions where the aggregates exist is closer than a distance threshold in the time-series images.

In a sixth aspect of the present invention, in the identifying the cell region, a region where the luminance of the first fluorescent protein in the time-series images exceeds a second luminance threshold different from the first luminance threshold may be identified as the region of the cell body of the neuron. In the detecting the aggregates, the presence or absence of the aggregates of the specific protein may be detected on the basis of a comparison between the luminance of the first fluorescent protein and the first luminance threshold in the region of the cell body identified in the identifying the cell region. In the performing the analysis, the neuron may be classified into a plurality of groups on the basis of a detection result of the presence or absence of the aggregates in the neurite and the presence or absence of the aggregates in the cell body in the detecting the aggregates, and the survival state of the neuron is analyzed for each of the groups.

In a seventh aspect of the present invention, in the identifying the cell region, the region of the cell body or the neurite of the neuron may be further identified on the basis of the time-series images obtained by imaging, in time series, second fluorescent protein expressed in the neuron and different from the first fluorescent protein. In the detecting the aggregates, whether the aggregates in the neurite identified exist in an axon or whether the aggregates exist in a dendrite may be detected on the basis of the first fluorescent protein and the second fluorescent protein. In the performing the analysis, on the basis of a detection result of the detecting the aggregates, the neuron may be classified into a cell group in which the aggregates in the neurite exist on a side close to the cell body and a cell group in which the aggregates exist on a side close to a terminal of the neurite, and the survival state of the neuron may be analyzed for each of the cell groups.

In an eighth aspect of the present invention, in the identifying the cell region, in images at respective time points included in the time-series images acquired in the time series, regions where luminance of the second fluorescent protein exceeds a luminance threshold may be extracted. In the identifying the cell region, a region exceeding a size threshold among the regions where the luminance exceeds the luminance threshold may be extracted to be identified as the region of the cell body of the neuron.

In a ninth aspect of the present invention, the method of analyzing neurons may further include performing association by specifying association between the cell body and the neurite constituting the neuron on the basis of the time-series images of the first fluorescent protein or the second fluorescent protein. The performing the analysis may include classifying the neuron into a plurality of groups on the basis of the detection result of the presence or absence of the aggregates in the neurite and the presence or absence of the aggregates in the cell body in the detecting the aggregates with respect to the cell body and the neurite associated in the performing the association, and analyzing the survival state of the neuron for each of the groups.

In a tenth aspect of the present invention, the survival state of the neuron may include at least one of survival or death, a survival period of time, or a survival rate of the neuron. The performing the analysis may include displaying, on a display unit, a relationship between the detection result of the presence or absence of the aggregates in the neurite and the presence or absence of the aggregates in the cell body detected in the detecting the aggregates and the survival state of the neuron.

In an eleventh aspect of the present invention, the performing the analysis may include determining, on the basis of the luminance of the first fluorescent protein included in the time-series images, that the neuron is dead if luminance of the neurite or the cell body of the neuron is less than the first luminance threshold or less than the second luminance threshold. The performing the analysis may include calculating, as a survival period of time of the neuron, a period of time until the luminance of the neurite or the cell body is in a state of less than the first luminance threshold or less than the second luminance threshold. The performing the analysis may include displaying, on a display unit, a relationship between the detection result of the presence or absence of the aggregates in the neurite and the presence or absence of the aggregates in the cell body detected in the detecting the aggregates and the survival period of time of the neuron.

In a twelfth aspect of the present invention, a device for analyzing neurons is provided. The device for analyzing neurons may include an imaging unit (may be referred to as an "imaging device") which acquires time-series images obtained by imaging a neuron in time series. The device for analyzing neurons may include an identification unit which identifies a region of a neurite or a region of a cell body of the neuron on the basis of the time-series images. The device for analyzing neurons may include a detection unit which detects, on the basis of the time-series images obtained by imaging, in time series, first fluorescent protein tagged to specific protein expressed in the neuron, presence or absence of aggregates of the specific protein aggregated in the region of the neurite or the region of the cell body of the neuron identified in the identification unit by using, as a basis, luminance of the first fluorescent protein included in the time-series images. The device for analyzing neurons may include an analysis unit which classifies the neuron into a plurality of groups on the basis of a detection result of the detection unit and analyzes a survival state of the neuron for each of the groups.

In a thirteenth aspect of the present invention, the survival state of the neuron may include at least any one of a survival period of time or a survival rate of the neuron. The analysis unit may display, for each of the groups, a relationship between the plurality of groups and survival states of the plurality of groups.

In a fourteenth aspect of the present invention, the identification unit may image, in time series, the first fluorescent protein tagged to the specific protein expressed in the neuron in the imaging unit. The identification unit may identify, as the region of the neurite of the neuron, a region where the luminance of the first fluorescent protein in the time-series images exceeds a first luminance threshold.

In a fifteenth aspect of the present invention, the identification unit may identify, as the region of the neurite or the cell body of the neuron, a region exceeding a predetermined size threshold among regions including the region where the luminance of the first fluorescent protein in the time-series images exceeds the first luminance threshold. The identification unit may track, in time series, each of the neurite being identified and identical and the cell body being identified and identical, and calculate a survival period of time related to the survival state.

In a sixteenth aspect of the present invention, the detection unit may detect the neurite region identified in the identification unit as a region where the aggregates of the specific protein exist. The detection unit may recognize, as one aggregate region, a plurality of the aggregates in which a distance between regions where the aggregates exist is closer than a distance threshold in the time-series images.

In a seventeenth aspect of the present invention, the identification unit may identify, as the region of the cell body of the neuron, a region where the luminance of the first fluorescent protein in the time-series images exceeds a second luminance threshold different from the first luminance threshold. The detection unit may detect the presence or absence of the aggregates of the specific protein on the basis of a comparison between the luminance of the first fluorescent protein and the first luminance threshold in the region of the cell body identified. The analysis unit may classify the neuron into a plurality of groups on the basis of a detection result of the presence or absence of the aggregates in the neurite and the presence or absence of the aggregates in the cell body in the detection unit, and analyze the survival state of the neuron for each of the groups.

In an eighteenth aspect of the present invention, the survival state of the neuron may include survival or death, a survival period of time, or a survival rate of the neuron. The analysis unit may display, on a display unit, a relationship between the detection result of the presence or absence of the aggregates in the neurite and the presence or absence of the aggregates in the cell body in the detection unit and the survival state of the neuron.

In a nineteenth aspect of the present invention, the analysis unit may determine, on the basis of luminance of the first fluorescent protein included in the time-series images or second fluorescent protein expressed in the neuron and different from the first fluorescent protein, that the neuron is dead if luminance of the neurite or the cell body of the neuron is less than the first luminance threshold or less than the second luminance threshold. The analysis unit may calculate, as a survival period of time of the neuron, a period of time until the luminance of the neurite or the cell body is in a state of less than the first luminance threshold or less than the second luminance threshold. The analysis unit may display, on a display unit, a relationship between the detection result of the presence or absence of the aggregates in the neurite and the presence or absence of the aggregates in the cell body in the detection unit and the survival period of time of the neuron.

In a twentieth aspect of the present invention, a computer program is provided. The computer program may include a computer-readable storage medium having therein instructions. The instructions, when executed by a processor or a programmable circuit, may cause the processor or the programmable circuit to perform operations including the method of analyzing neurons.

The summary clause does not necessarily describe all necessary features of the embodiments of the present invention. The present invention may also be a sub-combination of the features described above.

BRIEF DESCRIPTION OF THE DRAWINGS

FIG. 6A illustrates an example of a flow of tracking a cell body in S230 in the present embodiment.

DESCRIPTION OF EXEMPLARY EMBODIMENTS

Hereinafter, the present invention will be described through embodiments of the invention, but the following embodiments do not limit the invention according to claims. In addition, not all combination of the features described in the embodiments are necessary for the solution of the invention.

Figure 1:
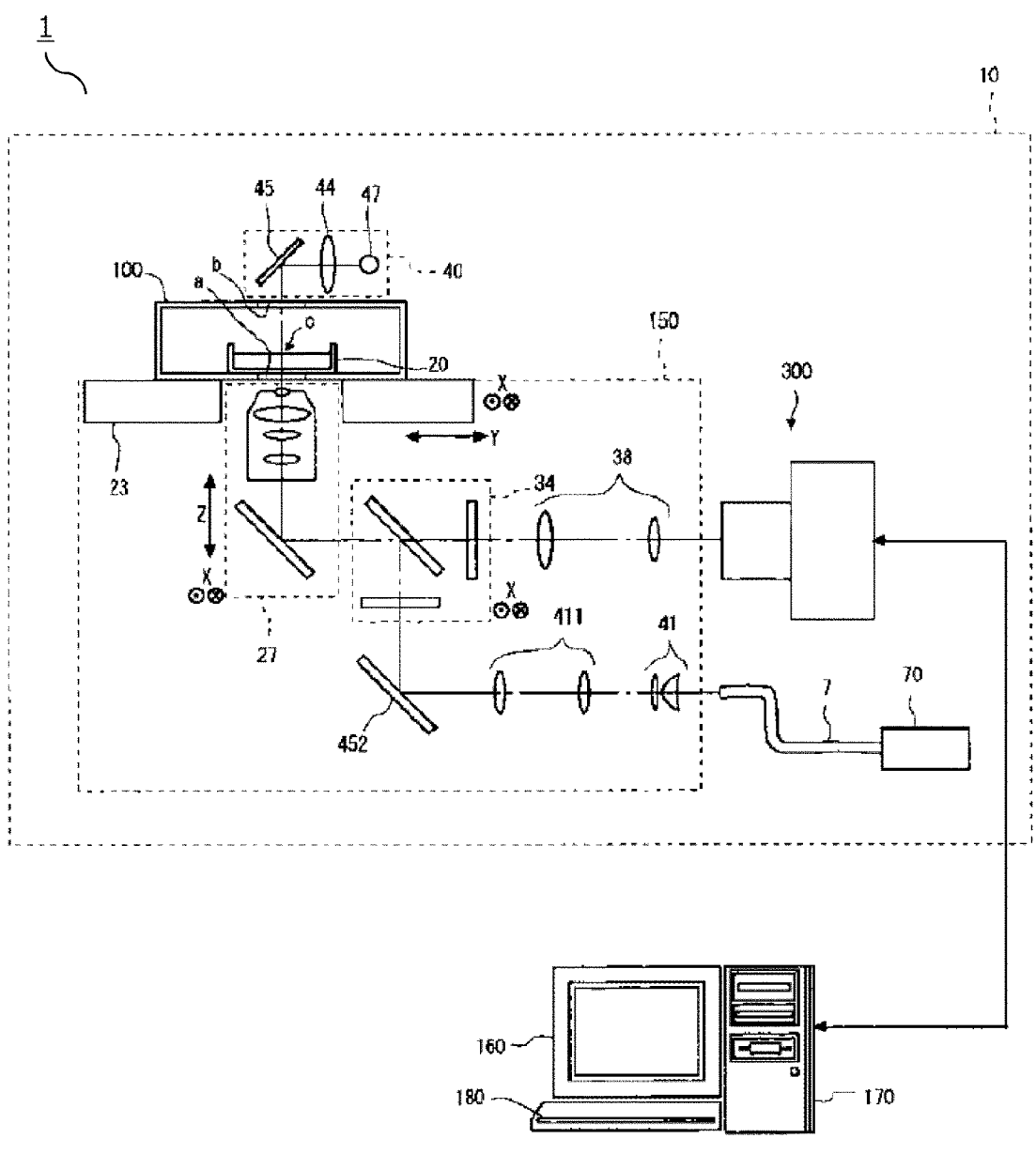
FIG. 1 illustrates an example of a device configuration of a device for analyzing neurons in the present embodiment.

FIG. 1 illustrates an example of a device configuration of a device for analyzing neurons in the present embodiment. A device for analyzing neurons 1 according to the present invention analyzes a relationship between the presence or absence of aggregates in a neurite region and/or a cell body region of a neuron and the state of the neuron such as survival or death, a survival period of time, and a survival rate of the neuron. Specifically, neurons may be classified into a plurality of cell groups on the basis of the result of an intra-cell body aggregate detection process and the result of an intra-neurite aggregate detection process (for example, may be classified into four cell groups as described later), and the state of the neurons may be analyzed for each for the cell groups. The device for analyzing neurons 1 may be placed in an environment in which neurons are cultured. For example, the device for analyzing neurons 1 may be provided in a $CO_2$ incubator in which temperature, humidity, and carbon dioxide concentration are adjusted. The device for analyzing neurons 1 includes an imaging device 10, an output unit 160, an arithmetic device 170, and an input unit 180.

The imaging device 10 is a device which images a neuron to generate an image of the neuron. The imaging device 10 captures observation images of the neuron a plurality of times in time series to generate a plurality of images. The imaging device 10 may include an optical fiber 7, a transmitted illumination unit 40, a light source for excitation 70, a microscope unit 150, and a camera 300.

The optical fiber 7 is a component which introduces a light emitted from the light source for excitation 70 into the microscope unit 150.

The transmitted illumination unit 40 is a light source unit used for phase difference observation of neurons. The transmitted illumination unit 40 includes a field lens 44, a polarized mirror 45, and a light source for transmitted illumination 47. The transmitted illumination unit 40 applies light transmitted through neurons.

The light source for excitation 70 is a light source used for fluorescence observation of neurons. The light source for excitation 70 applies, via the optical fiber 7 and the microscope unit 150, light to be reflected by neurons.

The microscope unit 150 is a device for enlarging and observing neurons by using a microscope. The neurons are not particularly limited, and may be established cells such as N1E-115 cells (mouse neuroblastoma) and PC-12 cells (rat pheochromocytoma), primary cultured cells collected from a cranial nerve tissue of a mouse, a rat, or the like, or neurons differentiated from embryonic stem cells (ES cells), induced pluripotent stem cells (iPS cells), or the like. For example, the neurons may be neurons differentiated from iPS cells derived from patients with neurodegenerative diseases. The microscope unit 150 may include a stage 23, an objective lens portion 27, a fluorescent filter portion 34, an imaging lens portion 38, a collector lens 41, a field lens 411, and a polarized mirror 452.

On the stage 23, a chamber 100 is mounted. The chamber 100 includes a transparent culture dish 20. The culture dish 20 is filled with a culture medium, and neurons are cultured in the culture medium. In order to observe a fluorescence image, the neurons may be labeled with one or more types of fluorescent substances (for example, fluorescent protein). A portion a of the bottom surface of the chamber 100 and a portion b of the upper surface of the chamber 100 may each be transparent. The upper surface of the chamber 100 may be opened or may be covered with a transparent lid. The upper surface or the bottom surface of the chamber 100 is transparent, or the upper surface of the chamber 100 is opened or covered with the transparent lid, so that a culture environment suitable for observing neurons can be provided.

To the chamber 100, a humidifier (not illustrated) may be connected via a silicone tube. With connection to the humidifier, the arithmetic device 170 to be described later can control the humidity and the carbon dioxide concentration inside the chamber 100 to be close to values suitable for culturing neurons. In addition, the chamber 100 may be provided with a temperature adjustment device (not illustrated) such as a heater or a cooler. For example, the temperature adjustment device may be an electric heater or a Peltier cooler. The temperature adjustment device is provided in the chamber 100, so that the temperature inside the chamber 100 can be controlled to be close to a value suitable for culturing neurons. Furthermore, a carbon dioxide gas cylinder may be connected to the chamber 100. With connection to the carbon dioxide gas cylinder, the pH of the culture medium in which neurons are cultured can be controlled to be close to a value suitable for culturing neurons. The humidity, the carbon dioxide concentration, and the temperature inside the chamber 100 are measured by a sensor (not illustrated). A measurement result is sent to the arithmetic device 170.

The objective lens portion 27 includes a plurality of objective lens in an x axis direction of FIG. 1 (a direction perpendicular to the paper surface). The objective lenses arranged in the optical path of the imaging device 10 are changed by moving the objective lens portion 27 in the x axis direction. Thus, the type and magnification of the objective lens can be changed.

The fluorescent filter portion 34 includes a plurality of types of filter blocks in the x axis direction of FIG. 1. The filter blocks arranged in the optical path of the imaging device 10 are changed by moving the fluorescent filter portion 34 in the x axis direction.

The camera 300 includes an imaging sensor (not illustrated). The camera 300 may be a cooling camera. The cooling camera is a camera that can cool the imaging sensor to suppress the noise generated by heat. The imaging sensor may be a CMOS imaging sensor (Complementary Metal Oxide Semiconductor) or a CCD imaging sensor (Charge Coupled Device). In addition, when adjusting the focus for imaging with the camera 300, the x coordinate and the y coordinate of the stage 23 and the z coordinate of the objective lens portion 27 may be controlled by the arithmetic device 170. The camera 300 may be housed in a housing different from the imaging device 10.

The output unit 160 outputs a processing result of the arithmetic device 170. For example, the output unit 160 may output a survival rate curve or the like of neurons which is an analysis result. For example, the output unit 160 may be a monitor connected to the arithmetic device 170. The output unit 160 may be referred to as a display unit.

The arithmetic device 170 is connected to the imaging device 10 and controls the imaging device 10. Specifically, the arithmetic device 170 changes the combination of the type of the objective lens of the objective lens portion 27 arranged in the optical path of the imaging device 10 and/or the type of the filter block of the fluorescent filter portion 34. For example, for the phase difference observation and the fluorescence observation, both the type of the filter block and the type of the objective lens that are arranged in the optical path are different. In addition, for a pair of two types of fluorescence observation, only the type of filter block arranged in the optical path is different. In addition, for the phase difference observation and the fluorescence observation, the used light source (the transmitted illumination unit 40 and the light source for excitation 70) are different. Therefore, in the inside (for example, an imaging device control unit 171 to be described later) of the arithmetic device 170, one or more of the filter block, the objective lens, and the light source may be changed according to which observation of the phase difference observation and the fluorescence observation is performed.

When phase difference observation is performed, the arithmetic device 170 turns on the light source for transmitted illumination 47 and turns off the light source for excitation 70 in order to enable the optical path of the transmitted illumination unit 40. When phase difference observation is performed, the light emitted from the light source for transmitted illumination 47 illuminates an observation position c of the culture dish 20 via the field lens 44, the polarized mirror 45, and the upper portion b of the chamber 100. The light transmitted through the observation position c reaches the light receiving surface of the camera 300 via the bottom surface of the culture dish 20, a bottom portion a of the chamber 100, the objective lens portion 27, the fluorescent filter portion 34, and the imaging lens portion 38. At this time, a phase difference image at the observation position c of the culture dish 20 is formed in the camera 300. The camera 300 is configured to capture the phase difference image and generate an image. The data of the generated image may be recorded in the arithmetic device 170 (for example, a recording unit 190 to be described later) and/or output to the output unit 160.

When fluorescence observation is performed, the arithmetic device 170 turns on the light source for excitation 70 and turns off the light source for transmitted illumination 47 in order to enable the optical path of the light source for excitation 70. When fluorescence observation is performed, the light emitted from the light source for excitation 70 illuminates the observation position c of the culture dish 20 via the optical fiber 7, the collector lens 41, the field lens 411, the polarized mirror 452, the fluorescent filter portion 34, the objective lens portion 27, the bottom portion a of the chamber 100, and the bottom surface of the culture dish 20. When the neuron cultured in the culture dish 20 is fluorescently labeled, the fluorescent substances of the neuron at the observation position c are excited and emit fluorescence. The fluorescence emitted from the neuron reaches the light receiving surface of the camera 300 via the bottom surface of the culture dish 20, the bottom portion a of the chamber 100, the objective lens portion 27, the fluorescent filter portion 34, and the imaging lens portion 38. At this time, a fluorescence image at the observation position c of the culture dish 20 is formed in the camera 300. The camera 300 is configured to capture the fluorescence image and generate an image. The data of the generated image may be recorded in the arithmetic device 170 (for example, a recording unit 190 to be described later) and/or output to the output unit 160.

Furthermore, in addition to the control of the imaging device 10, the arithmetic device 170 receives, from the imaging device 10, a plurality of images of the neuron captured by the imaging device 10, and analyzes, on the basis of the plurality of images, the relationship between the presence or absence of aggregates in the neurite region and/or the cell body region of the neuron and the state of the neuron such as the survival or death, the survival period of time, and the survival rate of the neuron. The configuration of the arithmetic device 170 will be described later.

The input unit 180 inputs, to the arithmetic device 170, an instruction, data, and the like from an observer. For example, the input unit 180 may input, to the arithmetic device 170, an instruction of the observer regarding a condition for imaging neurons and a condition for culturing neurons (the temperature, the humidity, the carbon dioxide concentration, and the like). In addition, the input unit 180 may input, to the arithmetic device 170, an instruction of the observer regarding a luminance threshold of the fluorescence and a condition of analysis of neurons. For example, the input unit 180 may be a keyboard or a mouse connected to the arithmetic device 170.

Figure 2:
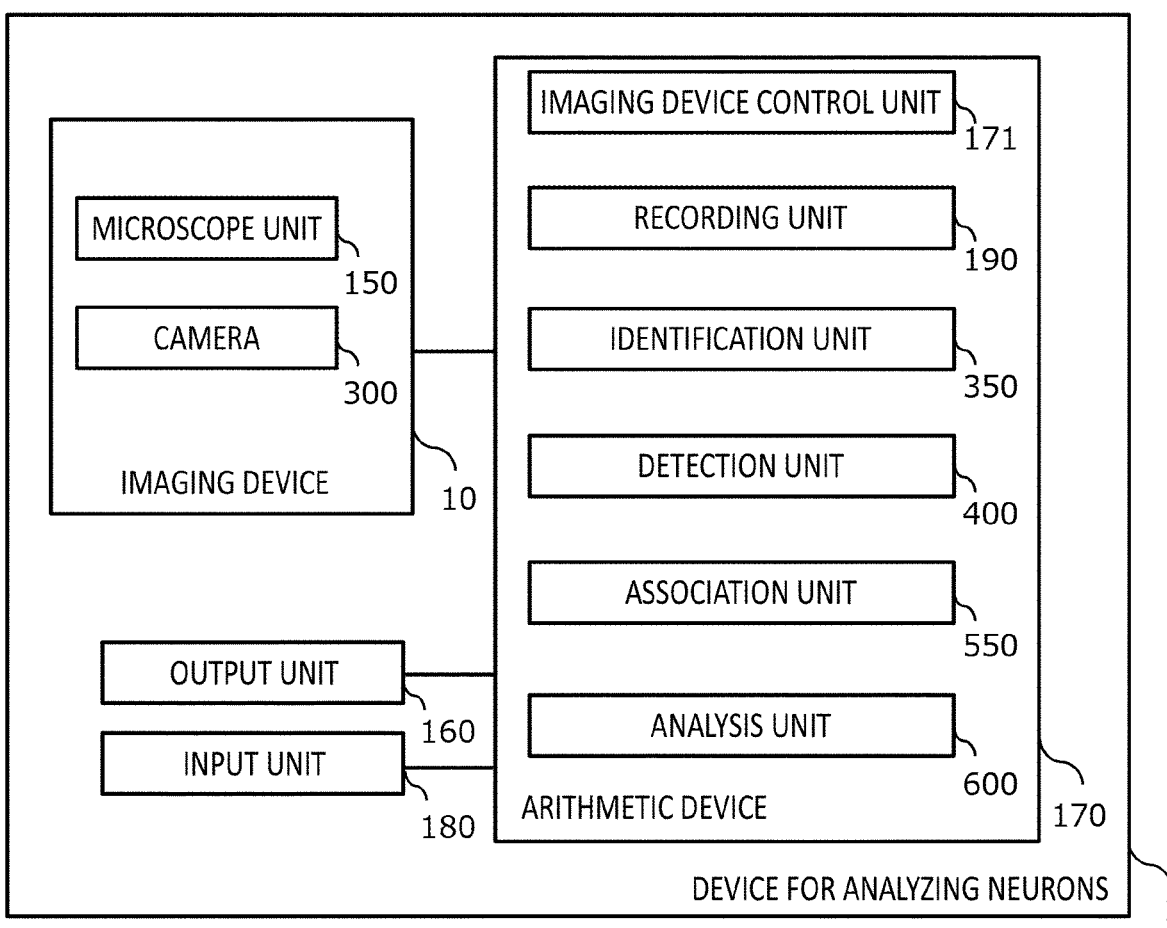
FIG. 2 illustrates an example of a specific configuration of the device for analyzing neurons in the present embodiment.

FIG. 2 illustrates an example of a specific configuration of the arithmetic device 170 in the present embodiment. The arithmetic device 170 includes the imaging device control unit 171, a recording unit 190, an identification unit 350, a detection unit 400, an association unit 550, and an analysis unit 600.

The imaging device control unit 171 controls the imaging device 10. For example, the imaging device control unit 171 controls the objective lens portion 27, the fluorescent filter portion 34, the transmitted illumination unit 40, the light source for excitation 70, the camera 300, and the like described in FIG. 1. As an example, when the imaging condition of neurons is input to the input unit 180 by the observer, according to the input imaging condition, the imaging device control unit 171 performs necessary adjustment among changing of the type of the objective lens of the objective lens portion 27 in the microscope unit 150, changing between the light source for transmitted illumination 47 and the light source for excitation 70, changing of the type of the fluorescence filter of the fluorescent filter portion 34, the position of the stage 23, and the height of the objective lens of the objective lens portion 27. After the imaging device control unit 171 performs necessary adjustment, the camera 300 images neurons and generates an image. The camera 300 transmits data of the generated image to the imaging device control unit 171. In addition, the data of the generated image may also be recorded in the recording unit 190 and/or output to the output unit 160.

The recording unit 190 stores an instruction and/or data necessary for the operation of the device for analyzing neurons 1. For example, the recording unit 190 may be a memory, a built-in hard disk drive, or an external recording medium, but is not limited thereto. The arithmetic device 170 includes a central processing unit (CPU), and the CPU executes a computer program recorded in the recording unit 190 to realize the imaging device control unit 171 or the like.

The identification unit 350 identifies a neurite region and/or a cell body region of a neuron in an image captured by the imaging device 10. Details of a method in which the identification unit 350 identifies the neurite region and/or the cell body region of the neuron will be described later.

The detection unit 400 detects the presence or absence of aggregates of protein aggregated in the neurite region and/or the cell body region identified by the identification unit 350. Details of a method in which the detection unit 400 detects the presence or absence of aggregates of protein aggregated in the neurite region and/or the cell body region will be described later. Note that the detection unit 400 may not be provided. In this case, the identification unit 350 detects the presence or absence of aggregates of protein aggregated in the neurite region and/or the cell body region.

Note that it is known that there are two types of neurites of a neuron: an axon and dendrites. The axon has a structure with a single elongated protrusion extending from a cell body of the neuron, and is responsible for outputting a signal in the neuron. The dendrites have a structure with a plurality of highly branched protrusions extending from the cell body of the neuron, and are responsible for inputting a signal in the neuron. In the present specification, the axon and the dendrite are collectively referred to as a neurite. In addition, in the cell body of a neuron, intracellular organdies such as a nucleus and ribosomes exist, where the axon and the dendrite converge.

The association unit 550 specifies association between a cell body and neurites constituting a neuron. Details of a method for specifying the association between a cell body and neurites of a neuron will be described later.

The analysis unit 600 analyzes a relationship between the result of determining the presence or absence of aggregates by the detection unit 400 and the state of the neuron. For example, the state of the neuron may be survival or death of the neuron. For example, the analysis unit 600 may analyze the relationship between the presence or absence of aggregates in the neurites and/or the cell body of the neuron and the survival or death of the neuron. For example, the analysis unit 600 may analyze at least one of the presence or absence of aggregates in the neurites and/or the cell body of the neuron, the survival period of the neuron, the persistence pattern of the aggregates in the neuron, the survival rate of the neuron, or the average survival period of the neuron. The analysis unit 600 may record an analysis result in the recording unit 190 and/or output it to the output unit 160.

Figure 3:
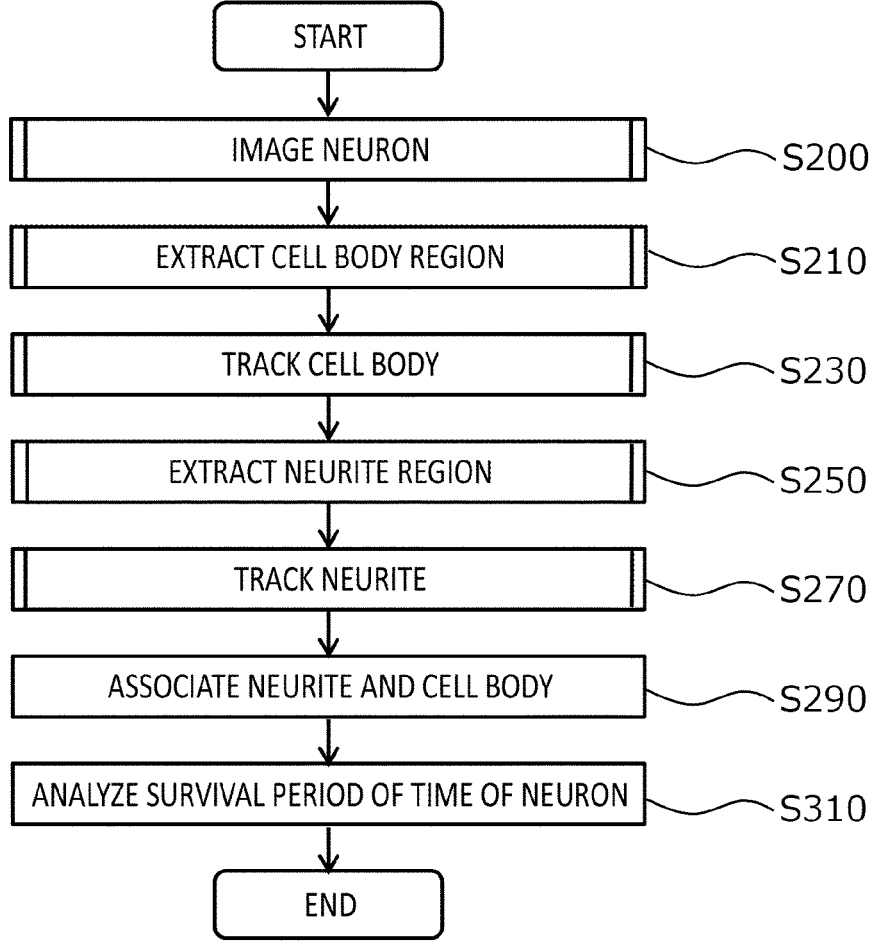
FIG. 3 illustrates an example of a flow of a method of analyzing neurons of the present embodiment.

FIG. 3 is an example of a flow of a method of analyzing neurons in the present embodiment. The state of the neuron of the present embodiment can be analyzed by performing the processing of S200 to S310 of FIG. 3. Note that, for convenience of description, the processing of S200 to the processing of S310 will be described in order; however, at least some processing may be executed in parallel, and each step may be interchanged and executed within a range not deviating from the spirit of the present invention.

First, in S200, the imaging device 10 images a neuron to generate a plurality of images (the step of S200 may be referred to as an "image acquisition process"). In S200, the step of imaging a neuron to generate a plurality of images includes steps of S201 to S206, as illustrated in FIG. 4.

Figure 4:
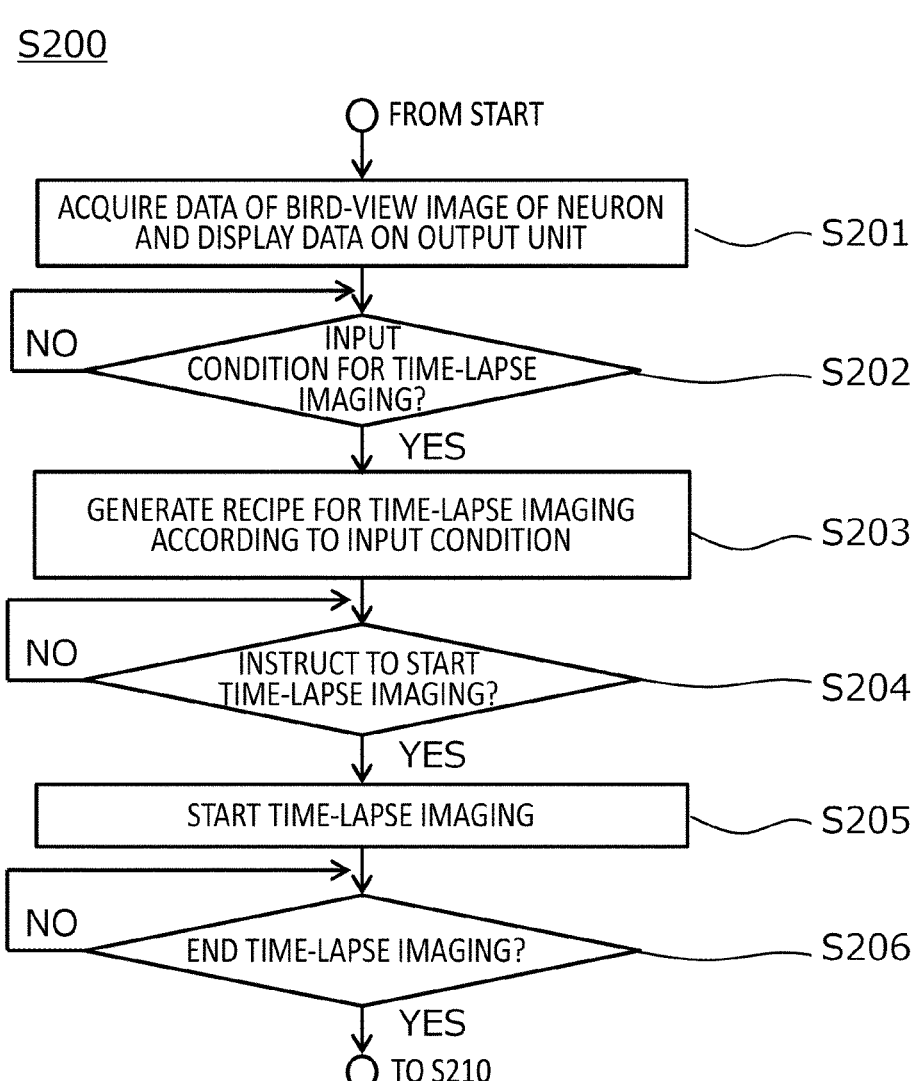
FIG. 4 illustrates an example of a flow of imaging neurons in S200 in the present embodiment.

FIG. 4 illustrates S200 in the flow. First, in S201, the culture dish 20 in which neurons are cultured is placed in the chamber 100. Placement of the culture dish 20 in the chamber 100 may be automatically performed by a robot (not illustrated), which has an articulated arm provided in the imaging device 10, receiving an instruction from the imaging device control unit 171, or may be performed by a hand of an observer. Next, the imaging device control unit 171 sets an observation method to low magnification phase difference observation, and the imaging device 10 images the neuron cultured in the culture dish 20 according to the instruction of the imaging device control unit 171. The low magnification phase difference observation may be performed by turning on the light source for transmitted illumination 47, turning off the light source for excitation 70, and moving the objective lens portion 27 in the x axis direction, to place the low magnification objective lens in the optical path of the imaging device 10. Thus, the imaging device 10 acquires a bird-view image, which is an image of a relatively wide region.

Alternatively, instead of the observation at a low magnification, a bird-view image may be acquired by acquiring a plurality of images (tile images) subjected to phase difference observation by the imaging device 10 while the imaging device control unit 171 moves the observation position c of the culture dish 20 in an xy plane, and synthesizing the images so as to form one image (synthesized image). The imaging device 10 may save the data of the acquired bird-view image in the recording unit 190 and/or output it to the output unit 160. After acquiring the bird-view image, the imaging device control unit 171 allows the processing to proceed to S202.

Next, in S202, the imaging device control unit 171 determines whether an input regarding a condition of time-lapse imaging has been received from the observer via the input unit 180. The condition of time-lapse imaging may be determined by the observer on the basis of the bird-view image output to the output unit 160. The condition of time-lapse imaging may be one or more of an interval, a round number, an observation position, and an observation method (phase difference observation or fluorescence observation), and may further include a condition regarding culture of neurons during imaging (for example, the composition, temperature, carbon dioxide concentration, humidity, and the like of the culture medium), but is not limited thereto. For example, when there are three types of observation methods (for example, phase difference observation, green fluorescence observation, and red fluorescence observation), the imaging device control unit 171 may continuously acquire three types of images while appropriately changing illumination, the filter block, and the objective lens. If the input regarding the condition of time-lapse imaging is received, the imaging device control unit 171 may allow the processing to proceed to S203. If the input regarding the condition of time-lapse imaging has not been received, the imaging device control unit 171 may allow the processing to return to S202 again, request the observer to input the condition of time-lapse imaging via the output unit 160, and stand by until the input is received.

Next, in S203, the imaging device control unit 171 may generate a recipe including the input condition of time-lapse imaging. The imaging device control unit 171 may record the generated recipe in the recording unit 190 and/or output it to the output unit 160. After the recipe generation, the imaging device control unit 171 allows the processing to proceed to S204.

Next, in S204, the imaging device control unit 171 determines whether an instruction to start the time-lapse imaging has been received from the observer via the input unit 180. If the instruction to start the time-lapse imaging is received, the imaging device control unit 171 may allow the processing to proceed to S205. If the instruction to start the time-lapse imaging has not been received, the imaging device control unit 171 may allow the processing to return to S204 again, request the observer to provide an instruction to start the time-lapse imaging via the output unit 160, and stand by until the instruction is received. Alternatively, if the instruction to start the time-lapse imaging has not been received, the imaging device control unit 171 may allow the processing to return to S204 again, request the observer to input the condition of time-lapse imaging different from the previously input condition via the output unit 160, and stand by until the input is made.

Next, in S205, the imaging device control unit 171 instructs the camera 300 to start time-lapse imaging of a neuron. The time-lapse imaging is performed in accordance with the recipe generated in S203. The imaging device control unit 171 adjusts the position of the stage 23 and/or the objective lens of the objective lens portion 27 such that the position of the observation position c of the culture dish 20 coincides with the observation position described in the recipe. Next, the camera 300 images the neuron and acquires an image, ending a first round of imaging.

Next, the imaging device control unit 171 instructs the camera 300 to stand by for an interval described in the recipe from a starting time of the first round of imaging in accordance with the generated recipe, and after that, to perform a second round of imaging in a similar way to the first round of imaging. In this manner, the camera 300 repeats the above-described imaging until the number of rounds described in the recipe is reached.

Next, in S206, if the number of rounds of the time-lapse imaging described in the recipe has been reached, the imaging device control unit 171 instructs the camera 300 to end imaging. If the number of rounds of the time-lapse imaging described in the recipe is not reached, the imaging device control unit 171 repeats the above-described imaging by the camera 300 until the designated number of rounds is reached.

During the time-lapse imaging, the imaging device control unit 171 accumulates data of images captured by the imaging device 10 in an implementation progress file. The imaging device control unit 171 records the implementation progress file in the recording unit 190. In addition, when an instruction of implementation progress check is input from the observer via the input unit 180 during or after the imaging of the time-lapse imaging, the imaging device control unit 171 may refer to the content of the implementation progress file at the time point of the input and output an implementation progress check screen to the output unit 160.

In addition, the imaging device control unit 171 may generate, as a moving image file, time-series images obtained by connecting images captured in respective rounds by the time-lapse imaging in time series for each observation method. For example, the imaging device control unit 171 may generate a moving image file of a phase difference image obtained by connecting a plurality of phase difference images in time series and/or generate a moving image file of a fluorescence image obtained by connecting a plurality of fluorescence images in time series. In addition to/instead of this, the imaging device control unit 171 may synthesize the phase difference image and the fluorescence image for each frame, and generate a moving image file of a synthesized image in which the frames after synthesizing are connected in time series. The imaging device control unit 171 may display the data of the time-series phase difference images (phase difference time-series images) captured by the imaging device 10, the data of the time-series fluorescence images (fluorescence time-series images), and/or the data including the generated moving image file on the output unit 160 and/or record them in the recording unit 190. After ending the time-lapse imaging, the imaging device control unit 171 allows the processing to proceed to S210 and/or S250. Note that some of the steps of S201 to S206 may be omitted without departing from the spirit of the present invention.

Here, the fluorescence emitted from the neuron may be derived from first fluorescent protein introduced in advance into the neuron. The first fluorescent protein may be obtained by attaching a tag (fluorescent tag) to the protein expressed in the neuron (neurites and/or cell body). The protein expressed in the neuron may be protein exhibiting aggregation propensity in the neuron.

The protein exhibiting aggregation propensity in the neuron may be α-synuclein protein, tau protein, prion protein, TDP-43 protein, huntingtin protein, or the like, but is not limited thereto. Here, the protein exhibiting aggregation propensity in the neuron may be referred to as "specific protein".

The α-synuclein protein is protein which is localized at an axon terminal of a neuron and consists of 140 amino acid residues. Although the physiological function of the α-synuclein protein is unknown, aggregates of the α-synuclein protein are observed in neurons in patients with Parkinson's disease or dementia with Lewy bodies, which suggests a possibility that the aggregation of α-synuclein protein causes pathology.

The tau protein is protein which is localized in an axon of a neuron and contributes to microtubule stability. In patients with Alzheimer's disease, aggregates of excessively phosphorylated tau protein are observed in neurons, which suggests a possibility that the aggregation of tau protein causes pathology.

The prion protein is protein which exists not only in nervous system tissue but also universally, but its physiological function is unknown. In patients with Creutzfeldt-Jakob disease, aggregates of prion protein are observed in a central nervous system, which suggests a possibility that the aggregation of prion protein causes pathology.

The TDP-43 protein is nuclear protein which exists not only in the nervous system but also universally, and is known to be involved in transcription and splicing. In patients with amyotrophic lateral sclerosis, aggregates of TDP-43 protein are observed in the central nervous system, which suggests a possibility that the aggregation of TDP-43 protein causes pathology.

The huntingtin protein is protein which exists not only in nervous system tissue but also universally and consists of 3145 amino acid residues. Although the physiological function of the huntingtin protein is unknown, aggregates of the huntingtin protein to which polyglutamine is abnormally added are observed in striatal neurons in patients with Huntington's disease, which suggests a possibility that aggregation of huntingtin protein causes pathology.

As mentioned above, the protein exhibiting aggregation propensity in neurons is a target for treating diseases. In the present invention, the relationship between the presence or absence of aggregates and the state of neuron (for example, the survival or death, the survival period of time, the survival rate, or the like of the neuron) can be analyzed by expressing, in the neuron, the first fluorescent protein obtained by adding a fluorescent tag to such protein. Here, the state of the neuron may be referred to as a "survival state of the neuron".

The fluorescent tag may be GFP, RFP, or the like, but is not limited thereto. The introduction of the first fluorescent protein into the neuron may be performed by introducing a plasmid vector or a viral vector (for example, adenovirus or the like) encoding the first fluorescent protein into the neuron.

Next, in S210, the identification unit 350 extracts, as the cell body region, a region exceeding a predetermined luminance threshold and a predetermined size threshold on the basis of the plurality of acquired fluorescence time-series images. The step of extracting, as the cell body region, the region exceeding the predetermined luminance threshold and the predetermined size threshold on the basis of the plurality of images in S210 includes steps of S211 to S215 as illustrated in FIG. 5A.

Figure 5A:
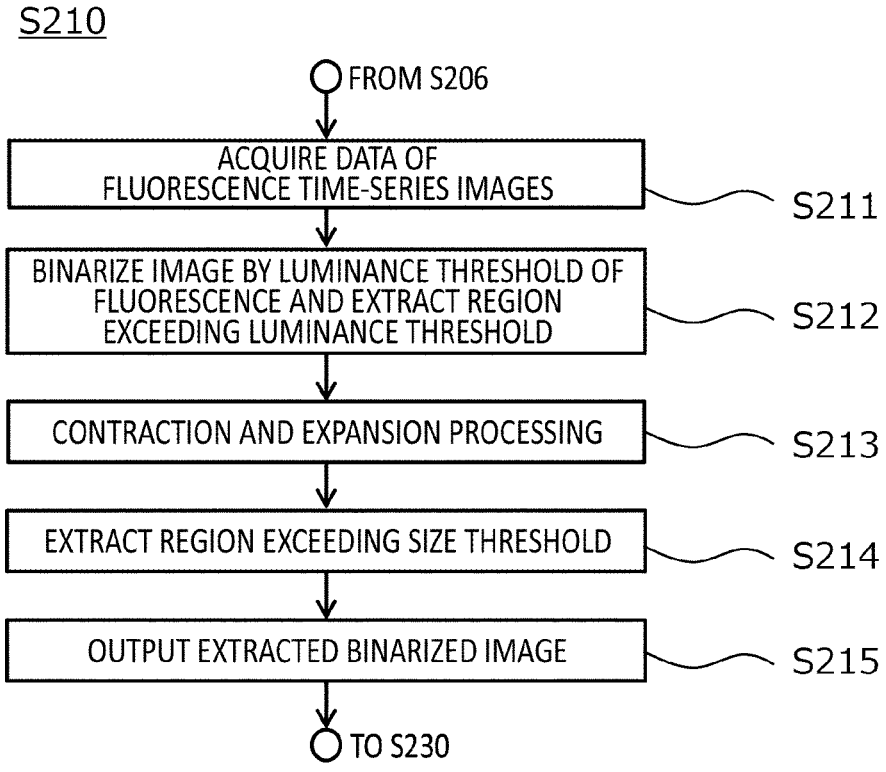
FIG. 5A illustrates an example of a flow of detecting a cell body region in S210 in the present embodiment.

FIG. 5A illustrates S210 in the flow. First, in S211, the data of the plurality of images captured by the imaging device control unit 171 is transmitted to the identification unit 350, so that the identification unit 350 acquires the data of the plurality of images. Here, the plurality of images may be fluorescence time-series images of the time-lapse imaging. After the identification unit 350 acquires the plurality of images, the identification unit 350 allows the processing to proceed to S212.

Next, in S212, the identification unit 350 binarizes the image with the luminance threshold of the fluorescence and extracts the region exceeding the luminance threshold. The luminance threshold may be designated by the observer. The identification unit 350 may receive an input regarding the luminance threshold from the observer via the input unit 180. Alternatively, the luminance threshold may be designated by the identification unit 350 on the basis of the plurality of acquired images.

Figure 5B:
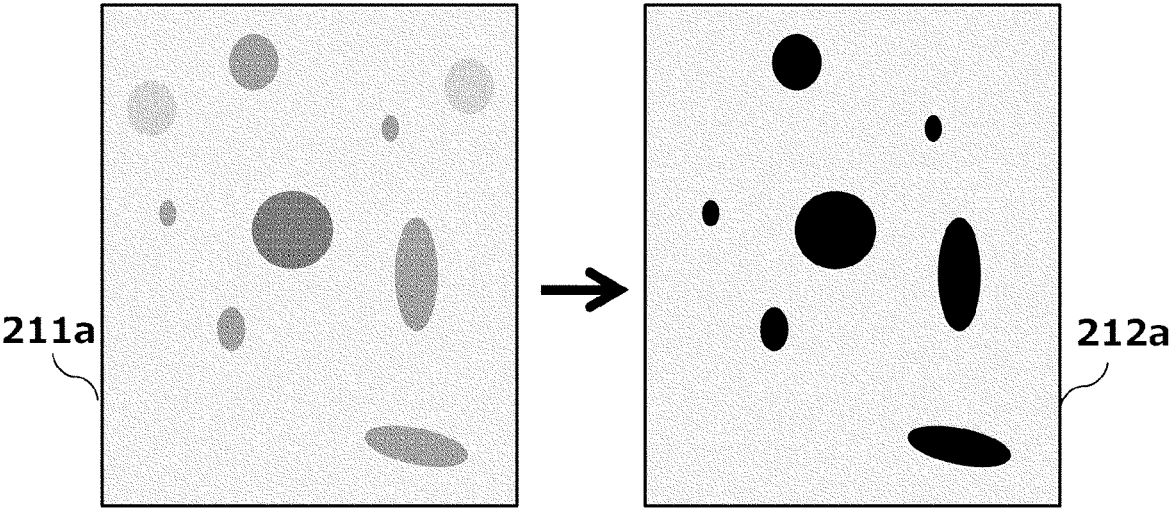
FIG. 5B illustrates an example of a flow of extracting a region (cell region) exceeding a luminance threshold in S212 in the present embodiment.

For example, in FIG. 5B, an image 211a is an example of an image captured by the imaging device 10. The luminance of the fluorescence is indicated by gray shading. At this time, the identification unit 350 extracts only a region having luminance equal to or higher than the luminance threshold. Specifically, if the luminance of a pixel in the image exceeds the luminance threshold, a predetermined luminance (for example, luminance 1) may be given to the pixel, and if the luminance of a pixel is equal to or less than the luminance threshold, luminance 0 may be given to the pixel. In this manner, a binarized image such as an image 212a can be acquired. After the identification unit 350 extracts the region exceeding the luminance threshold in the image, the identification unit 350 allows the processing to proceed to S213.

Next, in S213, the identification unit 350 performs contraction processing (erosion) and expansion processing (dilation) on the binarized image. The contraction processing and the expansion processing may be opening processing in which the contraction processing and the expansion processing are performed the same number of times. Specifically, the identification unit 350 first performs the contraction processing on the binarized image. Next, the identification unit 350 performs, on the image on which the contraction processing has been performed, the expansion processing the same number of times as the number of times the contraction processing has been performed. The contraction and expansion processing may be performed by the method described in Japanese Patent Application Publication No. 2018-198605. By performing the contraction processing and the expansion processing, it is possible to remove small noise or to separate a location where two regions are connected.

Figure 5C:
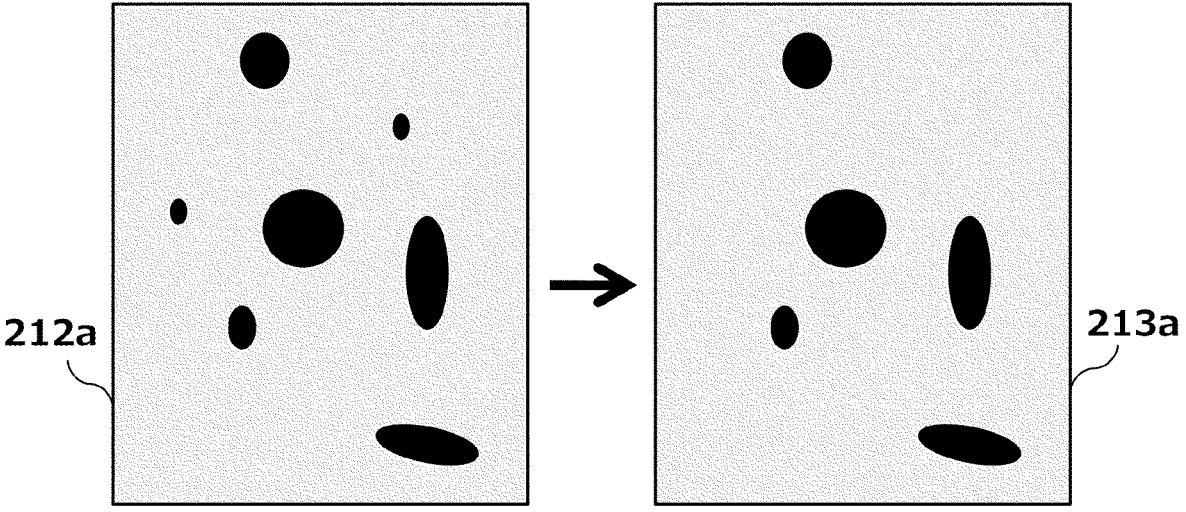
FIG. 5C illustrates an example of contraction and expansion processing in S213 in the present embodiment.

For example, in FIG. 5C, the identification unit 350 can acquire an image from which small noise has been removed as in the image 213a by performing the contraction and expansion processing on the binarized image 212a. After the identification unit 350 performs the contraction and expansion processing, the identification unit 350 allows the processing to proceed to S214. Note that the step of S213 may be omitted, and in this case, the identification unit 350 may allow the processing to proceed from S212 directly to S214.

Next, in S214, the identification unit 350 extracts, as the cell body region of the neuron, a region exceeding the size threshold from the image obtained by performing the contraction and expansion processing. The size threshold may be represented by the vertical and/or horizontal length of a quadrangle circumscribing a region in the image. The size threshold may be represented by the longer length of the vertical length or the horizontal length of a quadrangle circumscribing a region in the image, or may be represented by the shorter length thereof. The size threshold may be represented by the size of the area of a quadrangle circumscribing a region in the image. The size threshold may be designated by the observer. In this case, the identification unit 350 may receive an input regarding the size threshold from the observer via the input unit 180. Alternatively, the size threshold may be designated by the identification unit 350 on the basis of a plurality of acquired images. Furthermore, in addition to the circumscribing quadrangle, the size threshold may be defined by the length or the area of any circumscribing polygon, a circumscribing circle, or the like.

Figure 5D:
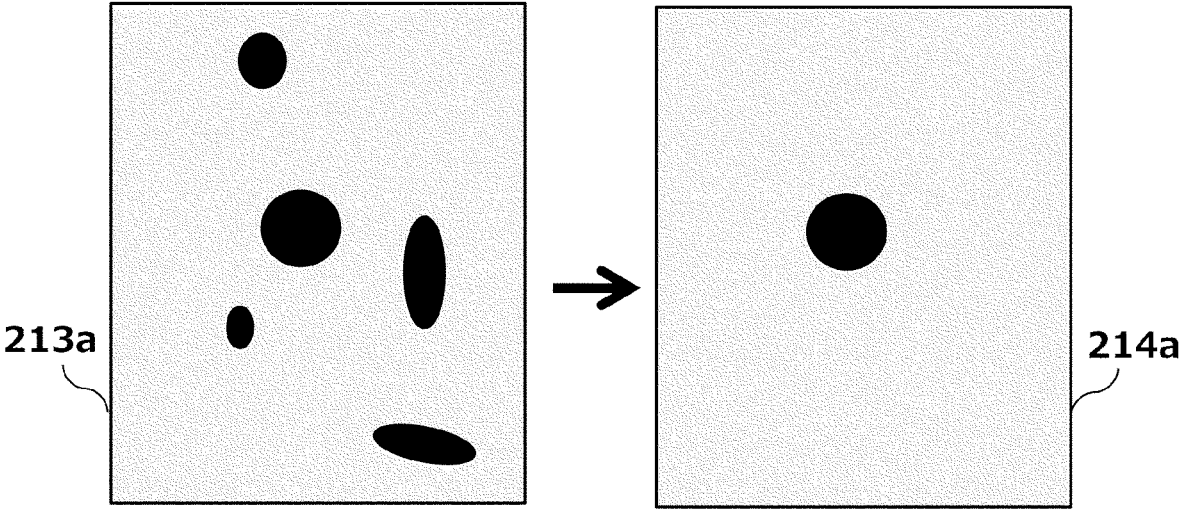
FIG. 5D illustrates an example of a flow of extracting a region exceeding a size threshold in S214 in the present embodiment.

For example, in FIG. 5D, the identification unit 350 can extract only the region exceeding the size threshold as in the image 214a by extracting a region, which has a size in which the vertical and horizontal lengths are equal to or larger than the designated length, in the image 213a subjected to the contraction and expansion processing.

The size threshold may include not only a lower limit value but also an upper limit value. Since the size threshold has the upper limit value and the lower limit value, the identification unit 350 can exclude a region which is either too large or too small to be regarded as a cell body, and extract, as a cell body, only a region in a specific size range. For example, when a place where the cell bodies of two or more neurons overlap each other is not suitable for analysis and it is desired to remove the place from the object to be analyzed, the upper limit value is set to the size threshold, so that it is possible to remove a region where the cell bodies of two neurons overlap each other and the size is increased. After the identification unit 350 extracts the region exceeding the size threshold, the identification unit 350 allows the processing to proceed to S215.

When the luminance of the fluorescence tends to increase with the lapse of time, the luminance threshold and/or the size threshold of the image captured at the previous time may be set to a value smaller than the luminance threshold and/or the size threshold of the image captured at the subsequent time. By setting in this way, a region having lower luminance and/or size can also be included in an analysis target.

Next, in S215, the identification unit 350 may save, in the recording unit 190, the image obtained by extracting the region exceeding the size threshold, and/or output it to the output unit 160. In addition, the identification unit 350 may output, to the association unit 550 and the analysis unit 600, the image obtained by extracting the region exceeding the size threshold.

Figure 5E:
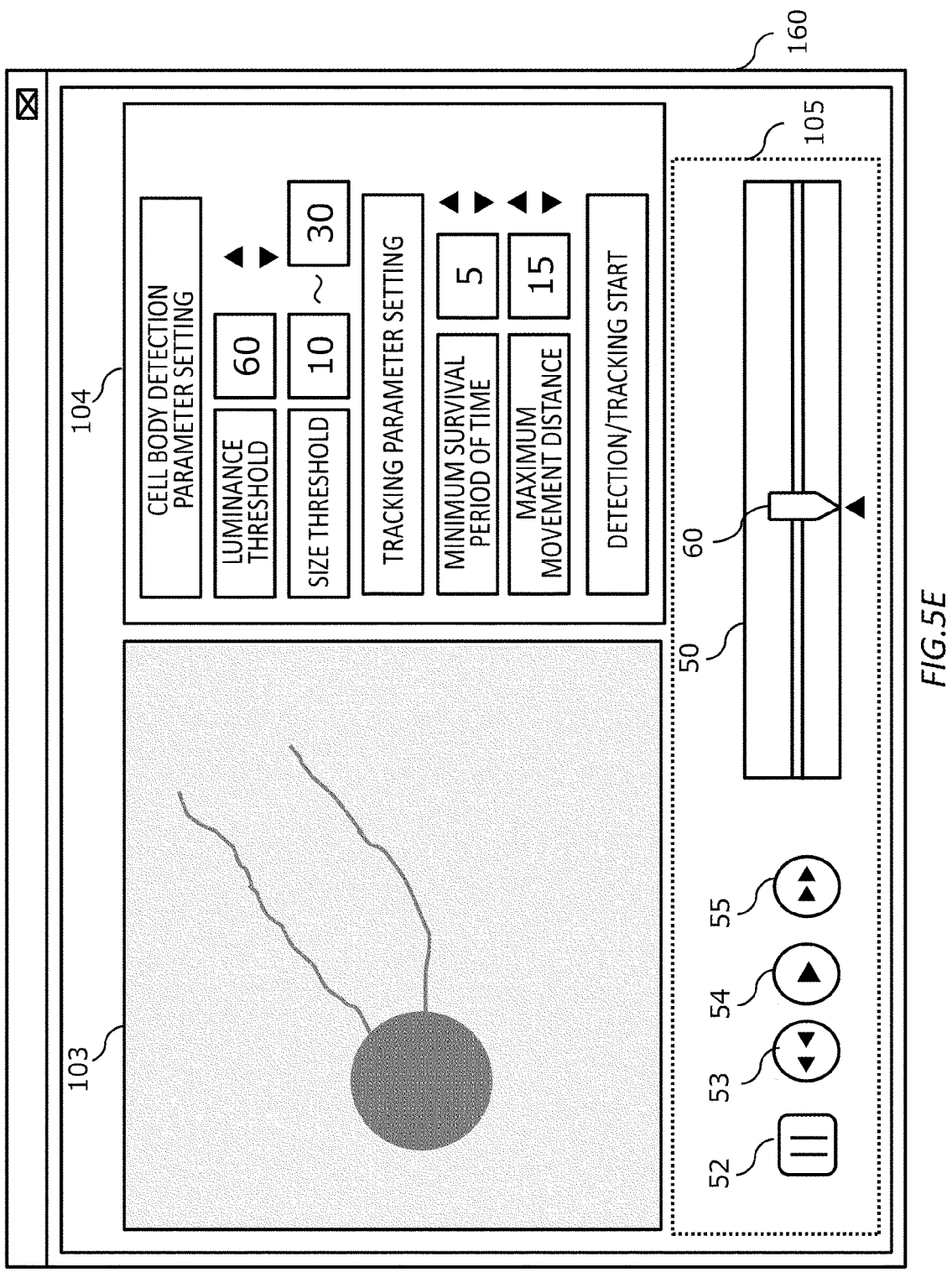
FIG. 5E illustrates an example of a screen displayed on an output unit of the device for analyzing neurons in the flow of detecting a cell body region in S210 in the present embodiment.

FIG. 5E is an example of a screen displayed on the output unit 160 by the identification unit 350 in order to cause the observer to designate the luminance threshold and/or the size threshold. In S212 and/or S214, the identification unit 350 may read the captured image file or moving image file simultaneously in parallel, generate an image signal for displaying the image on the output unit 160, and send the image signal to the output unit 160 in the order of generation, to display the image on a display region 103. A series of processing, which is performed by the identification unit 350, of reading the image file, generating the image signal, and sending the image signal will also be referred to as "playback of the moving image file".

A playback controlling portion 105 is a GUI (Graphic User Interface) image used by the observer to input an instruction regarding the playback of the moving image file. In the playback controlling portion 105, a timeline 50, a stop button 52, a fast-rewind button 53, a playback button 54, and a fast-forward button 55 may be arranged.

When the playback button 54 is selected by the observer via the input unit 180, the playback of the moving image file may be started, and the display of the moving image may be started on the display region 103. When the stop button 52 is selected by the observer, the playback of the moving image file is stopped. The playback point in a moving image file is reflected on the timeline 50. The left end of the timeline 50 represents the top of the moving image file, that is, the start time point of time-lapse imaging, and the right end of the timeline 50 represents the end of the moving image file, that is, the end time point of time-lapse imaging. When time-lapse imaging is not ended, the right end of the timeline represents the current time point.

On the timeline 50, a slider bar 60 is arranged. The slider bar 60 may represent the playback point in the moving image file in real-time. The position of the slider bar 60 in the horizontal direction may be capable of being moved freely by the observer. When the position of the slider bar 60 in the horizontal direction is moved by the observer, the playback point of the moving image file changes.

An appropriate luminance threshold and/or size threshold may be designated by the observer via the input unit 180. When the luminance threshold and/or the size threshold are designated by the observer, the display region 104 displays the designated luminance threshold and/or size threshold. Next, the identification unit 350 may perform a series of processing of S212 to S215 on the basis of the designated luminance threshold and/or size threshold, and display the processed image on the display region 103. From the processed image displayed on the display region 103, a new luminance threshold and/or size threshold may be further designated by the observer. The luminance threshold and/or the size threshold may be designated by the observer any number of times until a desired image is obtained.

In the above example, a case has been described in which the cell body region is specified on the basis of the fluorescence derived from the first fluorescent protein, but the cell body region may be specified on the basis of the image obtained by phase difference observation in addition to/instead of the fluorescence.

After the identification unit 350 outputs, to the association unit 550 and the analysis unit 600, the image obtained by extracting the region exceeding the size threshold, the identification unit 350 allows the processing to proceed to S230.

Next, in S230, the identification unit 350 tracks the cell body. In S230, the step of tracking the cell body includes the steps of S231 to S236, as illustrated in FIG. 6A.

FIG. 6A illustrates S230 in the flow. First, in S231, the identification unit 350 tracks a region between preceding and subsequent frames for a plurality of time-series images.

Figure 6B:
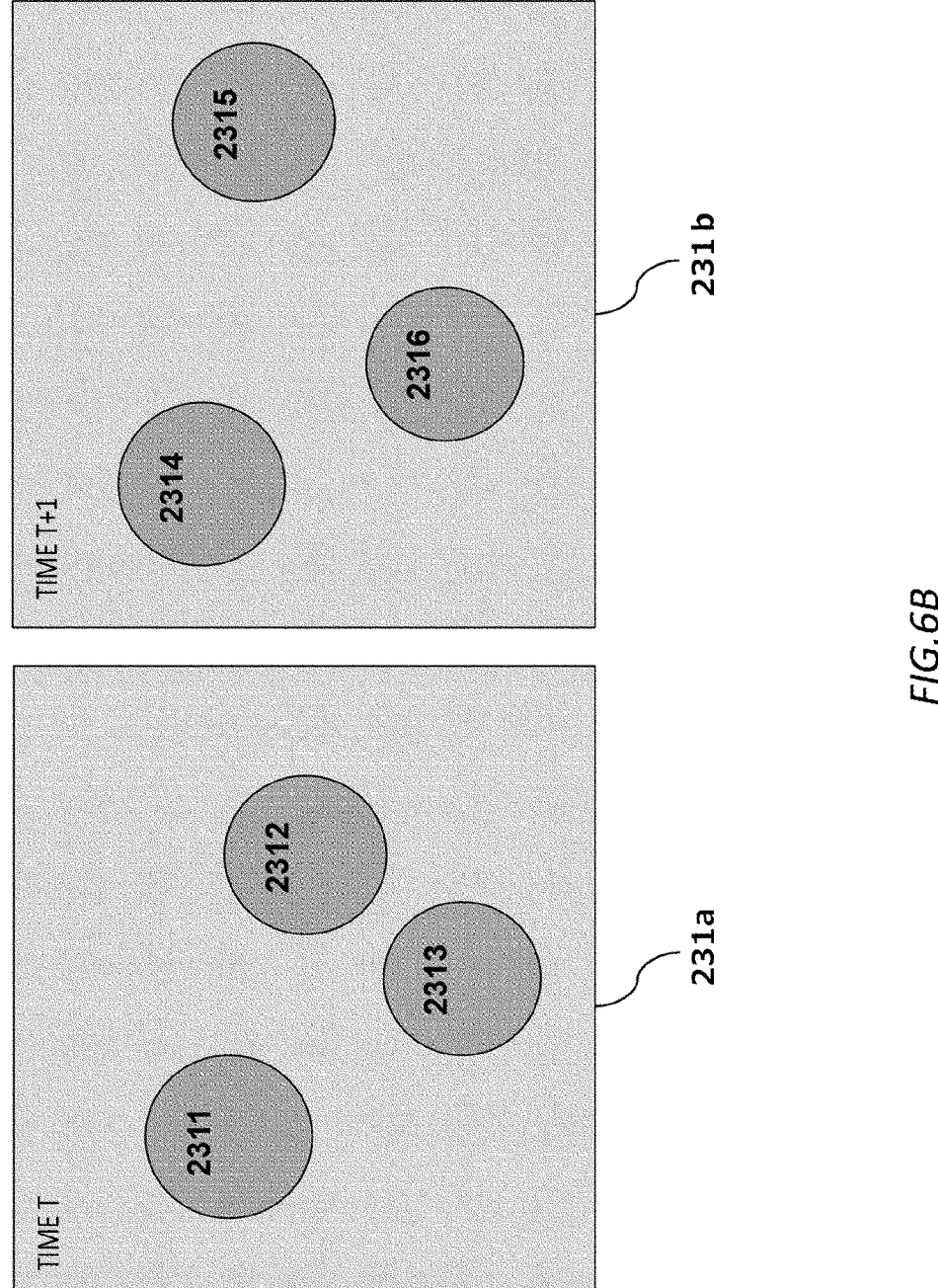
FIG. 6B illustrates an example of tracking a region between preceding and subsequent frames in S231 in the present embodiment.

FIG. 6B is an example of tracking a region between preceding and subsequent frames for the acquired time-series images. In imaging of neurons, the image captured in a round of time T is defined as an image 231a, and the image captured in a round of time T+1 immediately after time T is defined as an image 231b. In the image 231a, regions exceeding the luminance threshold (may be referred to as a "cell region(s)") is defined as a region 2311, a region 2312, and a region 2313, and in the image 231*b*, cell regions are defined as a region 2314, a region 2315, and a region 2316. At this time, the identification unit 350 may set a search range around the region corresponding to the region 2311 of the image 231*a* in the image 231*b*, and search for whether there is the region (that is, the cell region) corresponding to the region 2311 in the image 231*b*. Here, a quadrangle circumscribing the cell region (for example, a rectangle) is considered as the search region, and a quadrangle in which the vertical and horizontal lengths are increased little by little (for example, 5%, 10%, 20%, or the like of the vertical and horizontal lengths) from the end point may be set as the search region. Furthermore, in addition to the quadrangle, any polygon, circle, or the like may be set as the search region.

For example, the identification unit 350 may recognize that the cell region 2314, which is closer than a distance threshold set in advance as the search region, in the image 231*b* is the cell region corresponding to the region 2311 of the image 231*a*. That is, the identification unit 350 may recognize that the region 2311 and the region 2314 are the same cell body and perform tracking. Similarly, also for the region 2312 and the region 2313 of the image 231*a*, the identification unit 350 may search for whether there is a cell region in the search range set in the image 231*b* and perform tracking.

For example, if there is a plurality of cell regions in the search range of the image 231*b*, the identification unit 350 may recognize that a cell region closest to the search source region of the image 231*a* is the corresponding cell body region and track the cell region as the search source region of the image 231*a*. After the identification unit 350 tracks the region between the preceding and subsequent frames for all or some of the frames, the identification unit 350 allows the processing to proceed to S232.

Next, in S232, for the acquired time-series frames, the identification unit 350 tracks the cell region in a case where no cell body is detected in an intermediate frame. In the example of FIG. 6B, tracking is performed for two consecutive frames (for example, time T and time T+1), but the preceding and subsequent frames for tracking are not limited to two consecutive frames, and tracking may be performed for frames of distant time points within a predetermined period of time. The identification unit 350 executes the processing of S231 and S232 for all rounds. For example, the identification unit 350 repeatedly executes the tracking from the first round (that is, time T is 1) to the last round (that is, time T is N which is the number of rounds for imaging).

In imaging of neurons, there may be a case where the cell region corresponding to the cell region detected in the round of time T does not exist in the round of time T+1. In this case, the identification unit 350 may further set, in the image of the round of time T+2 immediately thereafter, the search region around the cell region detected in the round of time T. That is, in the image captured in the round of time T+2 immediately after the time T+1, a cell region closer than the distance threshold set in advance as the search region may be recognized as the same cell body and tracked. If a plurality of cell regions exist in the search region, the cell closest to the search source region may be recognized as the same cell body and tracked. After the identification unit 350 tracks the cell region in a case where no cell body is detected in the intermediate frame, the identification unit 350 allows the processing to proceed to S2320. A result of tracking for each cell body in S232 is hereinafter also referred to as a "tracking result". Note that, in the above example, an example of tracking the cell region detected in the round of time T and the cell region in the image captured in the round of time T+2 has been described, but the present invention is not limited to the round of time T+2, and for example, the cell region in the image captured in the round of time T+3, the time T+4, or the like may be tracked as the cell region detected in the round of time T.

Next, in S2320, the identification unit 350 detects the time of starting the tracking of the cell body and the time of ending the tracking. For example, for each cell body tracking result, the identification unit 350 may output, to the analysis unit 600, the time at which the tracking of each cell body has started (also referred to as "tracking start time") and the time at which the tracking has ended (also referred to as "tracking end time"), save them in the recording unit 190, and/or output them to the output unit 160. Here, the time at which the tracking of the cell body is started may be the time of a frame, at which the cell body first emits fluorescence having luminance equal to or higher than the threshold, in the captured image, and the end time of the tracking may be the time of a frame, at which the luminance of the cell body becomes less than the luminance threshold, in the captured image. The tracking end time may be determined as a timing, at which cell death of the neuron occurs, by the identification unit 350. After the identification unit 350 detects the start and end times of the tracking of the cell body, the identification unit 350 allows the processing to proceed to S233.

Next, in S233, the detection unit 400 deletes the tracking result of the cell body found to have moved a distance equal to or longer than the threshold as a result of the tracking in S232 performed by the identification unit 350. The detection unit 400 may judge whether the cell body has moved a distance equal to or longer than the threshold for frames of separated time points within a predetermined period of time. With this processing, the detection unit 400 can exclude a cell body, which has moved beyond an assumed distance, as a cell body which has failed in tracking.

For example, the detection unit 400 may use a center of gravity, a center, an end portion, or the like of the cell region as a reference of the movement distance of the cell region. For example, the detection unit 400 may place the cell region on an xy coordinate plane, calculate averages $x_{mean}$ and $y_{mean}$ of the coordinate values of all the pixels included in the cell region for the x axis direction and the y axis direction, respectively, and define an obtained point ($x_{mean}$, $y_{mean}$) as the center of gravity. For example, the detection unit 400 may place the cell region on the xy coordinate plane, calculate $x_{ave}$ which is the average value of the minimum value and the maximum value of the cell region on the x axis, similarly calculate $y_{ave}$ which is the average value of the minimum value and the maximum value of the cell region on the y axis, and define an obtained point ($x_{ave}$, $y_{ave}$) as the center. For example, the detection unit 400 may place the cell region on the xy coordinate plane, and define, as the end portion, a point located at an end on the x axis or the y axis in a predetermined direction (+ direction or − direction) among points on the outer periphery of the cell region.

For example, if a movement distance of a cell region in the period of time between two consecutive frames (for example, time T and time T+1) is equal to or longer than twice the size threshold used in S214, the detection unit 400 may determine that the tracking of the cell body included in the cell region has failed and delete the tracking result of the cell body including the two frames. In addition, in the above example, the movement distance is twice as long as the size threshold, but the movement distance may be 3 times or 0.5 times as long as the size threshold, and is not limited thereto. Thus, the cell region is excluded from the analysis target of the analysis unit 600 to be described later. If the neuron to be observed is a cell having poor mobility, artifacts can be excluded by performing the step of S233.

For example, on the screen of FIG. 5E, the detection unit 400 may display, on the output unit 160, the display region 104 for inputting a threshold of the movement distance, and request the observer to input the threshold of the movement distance. An appropriate threshold of the movement distance may be designated by the observer via the input unit 180. On the basis of the designated threshold of the movement distance, the detection unit 400 may delete the tracking result of the cell body found to have moved a distance equal to or longer than the threshold. After the detection unit 400 deletes the tracking result of the cell body having the movement distance equal to or longer than the threshold, the detection unit 400 allows the processing to proceed to S234.

Next, in S234, the detection unit 400 deletes the tracking result in which the survival period of time is equal to or less than the threshold. The detection unit 400 deletes the tracking result of the cell body identification unit found to have the survival period of time equal to or less than the threshold as a result of the tracking in S232. Here, the survival period of time may be a period of time between the time when the tracking of the cell body is started and the time when the tracking is ended.

For example, on the screen of FIG. 5E, the detection unit 400 may display, on the output unit 160, the display region 104 for inputting a threshold of the survival period of time, and request the observer to input the threshold of the survival period of time. An appropriate threshold of the survival period of time may be designated by the observer via the input unit 180. On the basis of the designated threshold of the survival period of time, the detection unit 400 may delete the tracking result of the cell body having the survival period of time equal to or less than the threshold. After the detection unit 400 deletes the tracking result of the cell body having the survival period of time equal to or less than the threshold, the detection unit 400 allows the processing to proceed to S235.

Next, in S235, the detection unit 400 assigns an ID to the tracking result of the cell body in the image acquired in S215, and outputs the result. The detection unit 400 assigns a unique ID (cell body ID) to the tracking result of each cell body tracked between the acquired time-series frames. That is, the tracking results assigned with the same cell body ID represent the same cell body. For example, in FIG. 6B, the detection unit 400 may regard the region 2311 and the region 2314 as regions have the same cell body and assign the same cell body ID thereto. The detection unit 400 outputs the cell body ID together with the image to the association unit 550. In addition, the detection unit 400 may save the cell body ID in the recording unit 190 and/or output it to the output unit 160. After the detection unit 400 assigns the ID to the tracking result of the cell body and outputs the result, the detection unit 400 allows the processing to proceed to S236.

In S236, the detection unit 400 determines that the region extracted in the steps of S231 to S235 is the cell body region. Next, by using a luminance threshold different from the luminance threshold used in the step of S212, the detection unit 400 may perform a step of determining that the region exceeding the luminance threshold is a region where aggregates exist, that is, a region where aggregates exist inside the cell body (may be referred to as "intra-cell body aggregate region") and extracting the region. Specifically, the luminance threshold for extracting the intra-cell body aggregate region used in S236 may be larger than the luminance threshold for extracting the cell body region used in S212. The step of S236 performed by the detection unit 400 may be referred to as a second aggregate detection process (step), that is, a step of detecting aggregates existing inside the cell body.

By performing the above steps of S211 to S236, the detection unit 400 may determine the cell body region and the intra-cell body aggregate region (the determination of the detection unit 400 on them may be referred to as a "cell region identification process" and an "aggregate detection process", respectively).

In the above example, the detection unit 400 extracts the cell region exceeding the luminance threshold and the size threshold, but the detection unit 400 may extract the region by using only the luminance threshold.

Figure 7A:
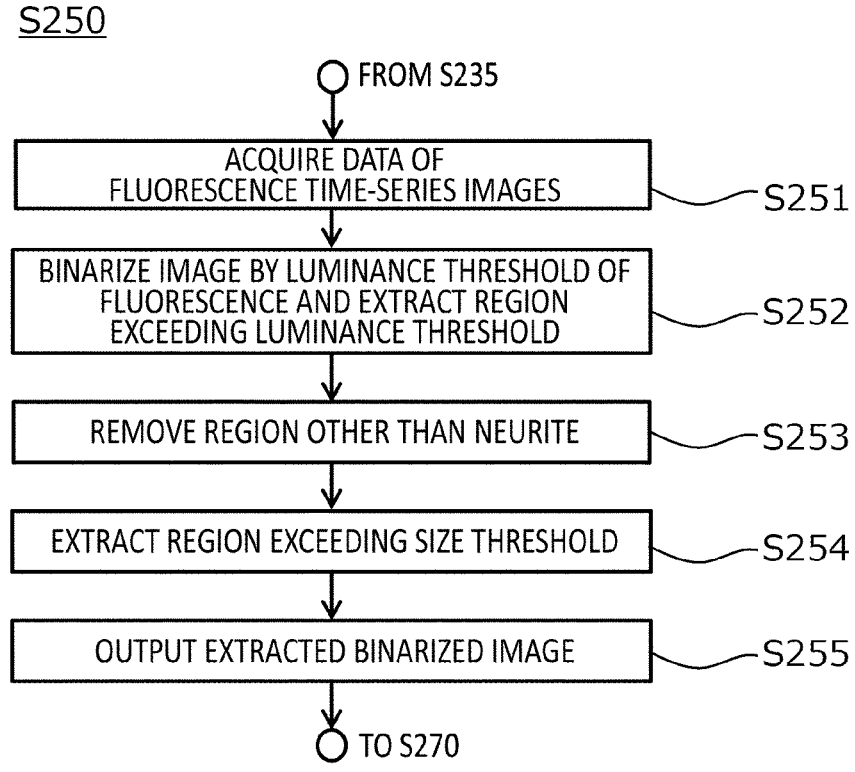
FIG. 7A illustrates an example of a flow of detecting a neurite region in S250 in the present embodiment.

In S250, the identification unit 350 extracts, as the neurite region, a region exceeding a predetermined luminance threshold and a predetermined size threshold on the basis of the plurality of acquired fluorescence time-series images. The step of extracting, as the neurite region, the region exceeding the luminance threshold and the size threshold on the basis of the plurality of images in S250 includes steps of S251 to S255 as illustrated in FIG. 7A. Note that "extraction" may be referred to as "identification".

FIG. 7A illustrates S250 in the flow. First, in S251, the data of the plurality of images captured by the imaging device control unit 171 is transmitted to the identification unit 350, so that the identification unit 350 acquires the data of the plurality of images. Here, the plurality of images may be fluorescence time-series images of the time-lapse imaging. Note that, when S211 is performed before the step of S251, the step of S251 may be omitted. After the identification unit 350 acquires the plurality of images, the identification unit 350 allows the processing to proceed to S252.

Next, in S252, the identification unit 350 binarizes the image with the luminance threshold of the fluorescence and extracts the cell region. The luminance threshold may be designated by the observer. The identification unit 350 may receive an input regarding the luminance threshold from the observer via the input unit 180. Alternatively, the luminance threshold may be designated by the identification unit 350 on the basis of the plurality of acquired images. The luminance threshold in S212 processed by the identification unit 350 and the luminance threshold in S252 may be the same as or different from each other. In this case, when the luminance thresholds of S212 and S252 are the same, the step of S252 may be omitted.

Figure 7B:
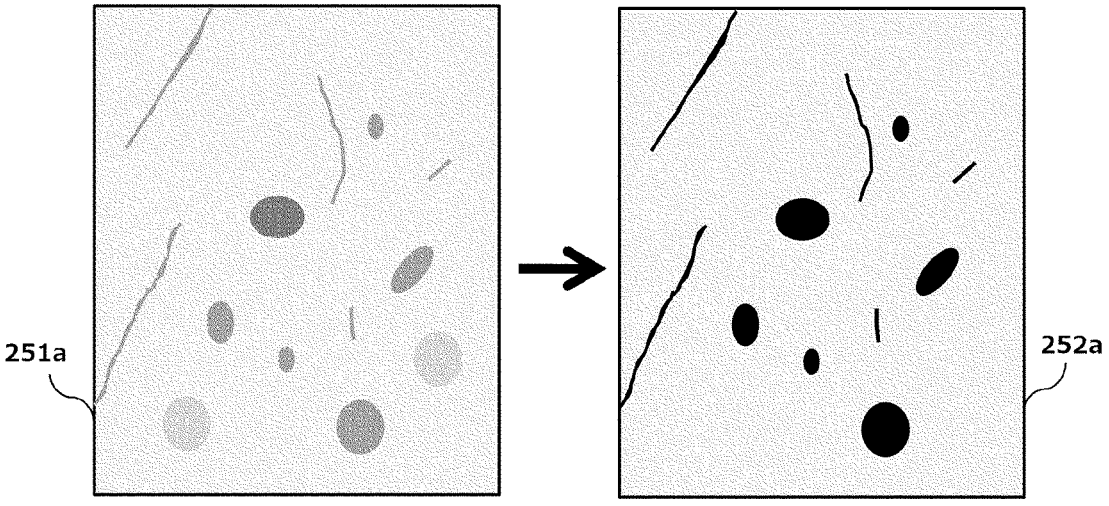
FIG. 7B illustrates an example of the flow of detecting a neurite region in S250 in the present embodiment.

For example, in FIG. 7B, an image 251a is assumed to be an image captured by the imaging device 10. The luminance of the fluorescence is indicated by gray shading. At this time, the identification unit 350 extracts only a region (cell region) having luminance equal to or higher than the luminance threshold. Specifically, if the luminance of a pixel in the image exceeds the luminance threshold, a predetermined luminance (for example, luminance 1) may be given to the pixel, and if the luminance of a pixel is equal to or less than the luminance threshold, luminance 0 may be given to the pixel. In this manner, an image, in which luminance is binarized, as an image 252a can be acquired. After the identification unit 350 extracts the cell region in the image, the identification unit 350 allows the processing to proceed to S253.

Next, in S253, the identification unit 350 removes cell regions (for example, cell bodies and noise) other than neurites in the binarized image. For example, as a first removal method, the cell regions other than neurite are removed by removing the cell bodies. That is, in order to detect only the cell regions of the neurites, the cell regions of the cell bodies or the like may be removed by excluding the cell body image (for example, pixels with a luminance threshold of 60 and a size threshold of 10) from the image binarized with a luminance threshold of 150.

In addition, as a second removal method, a method of removing a cell region other than neurites in a binarized image may be performed by a method described in Japanese Patent Application Publication No. 2004-163201. Specifically, the identification unit 350 extracts the cell body region detected in S210, removes the extracted cell body region from the original binarized image, and extracts the neurite region through thinning processing and noise removal processing. Specifically, in a cell protrusion extraction method for extracting only a neurite region from an image, binarization processing is performed on the acquired image to acquire a binarized image, and a cell body region is extracted from a compressed image (DC component) obtained by performing wavelet transform processing on the binarized image. Then, the extracted cell body region is removed from the binarized image, and an image mainly including a line element is acquired. The image from which the cell body region has been removed may be subjected to the thinning processing to obtain a thinned image in which the line element has a line width of one pixel, and then subjected to the noise removal processing to obtain an image of only the neurite region.

Here, the thinning processing is processing of obtaining a thinned image in which a line element has a line width of one pixel. The noise removal processing is processing of removing a region having a small area corresponding to noise. After the identification unit 350 removes the regions other than the neurite, the identification unit 350 allows the processing to proceed to S254. Note that the step of S253 may be omitted, and in this case, the identification unit 350 may allow the processing to proceed from S252 directly to S254.

Next, in S254, the identification unit 350 extracts, as the neurite region of the neuron, a region exceeding a size threshold from the image obtained by removing the cell regions other than the neurite. The size threshold may be represented by the vertical and/or horizontal length of a quadrangle circumscribing a cell region in the image. The size threshold may be represented by the longer length of the vertical length or the horizontal length of a quadrangle circumscribing a region in the image, or may be represented by the shorter length thereof. The size threshold may be represented by the size of the area of a quadrangle circumscribing a cell region in the image. The size threshold may be designated by the observer. In this case, the identification unit 350 may receive an input regarding the size threshold of the cell region from the observer via the input unit 180. Alternatively, the size threshold may be designated by the identification unit 350 on the basis of a plurality of acquired images. The size threshold in S214 processed by the identification unit 350 and the size threshold in S254 may be the same as or different from each other. Furthermore, in addition to the circumscribing quadrangle, the size threshold may be defined by the length or the area of any circumscribing polygon, a circumscribing circle, or the like.

The size threshold may include not only a lower limit value but also an upper limit value. Since the size threshold has the upper limit value and the lower limit value, the identification unit 350 can exclude a region which is either too large or too small to be regarded as a neurite, and extract, as a neurite, only a cell region in a specific size range. For example, when a place where the neurites of two neurons overlap each other is not suitable for analysis and it is desired to remove the place from the object to be analyzed, the upper limit value is set to the size threshold, so that it is possible to remove a location which becomes large since the neurites of the two neurons overlap each other. After the identification unit 350 extracts the region exceeding the size threshold, the identification unit 350 allows the processing to proceed to S255.

At the time of protrusion identification, the identification unit 350 may set different luminance thresholds and/or size thresholds depending on the position in the image. For example, in an image captured in a round of a certain time T, a threshold A can be used at a position corresponding to a region extracted in an image captured in a round of a time T−1 immediately before the round, and a threshold B can be used at a position not corresponding to the extracted region. Here, the threshold A may be set as a value smaller than the threshold B. Since there is a high possibility that the neurite is present at the same position at a subsequent time when the neurite exists at a previous time, by setting in this way, a reference for detecting only the position can be relaxed, and a cell region having lower luminance and/or size can also be included in the analysis target.

Next, in S255, the identification unit 350 may save, in the recording unit 190, the image obtained by extracting the region exceeding the size threshold, and/or output it to the output unit 160. In addition, the identification unit 350 may output, to the association unit 550 and the analysis unit 600, the image obtained by extracting the cell region exceeding the size threshold.

Figure 7C:
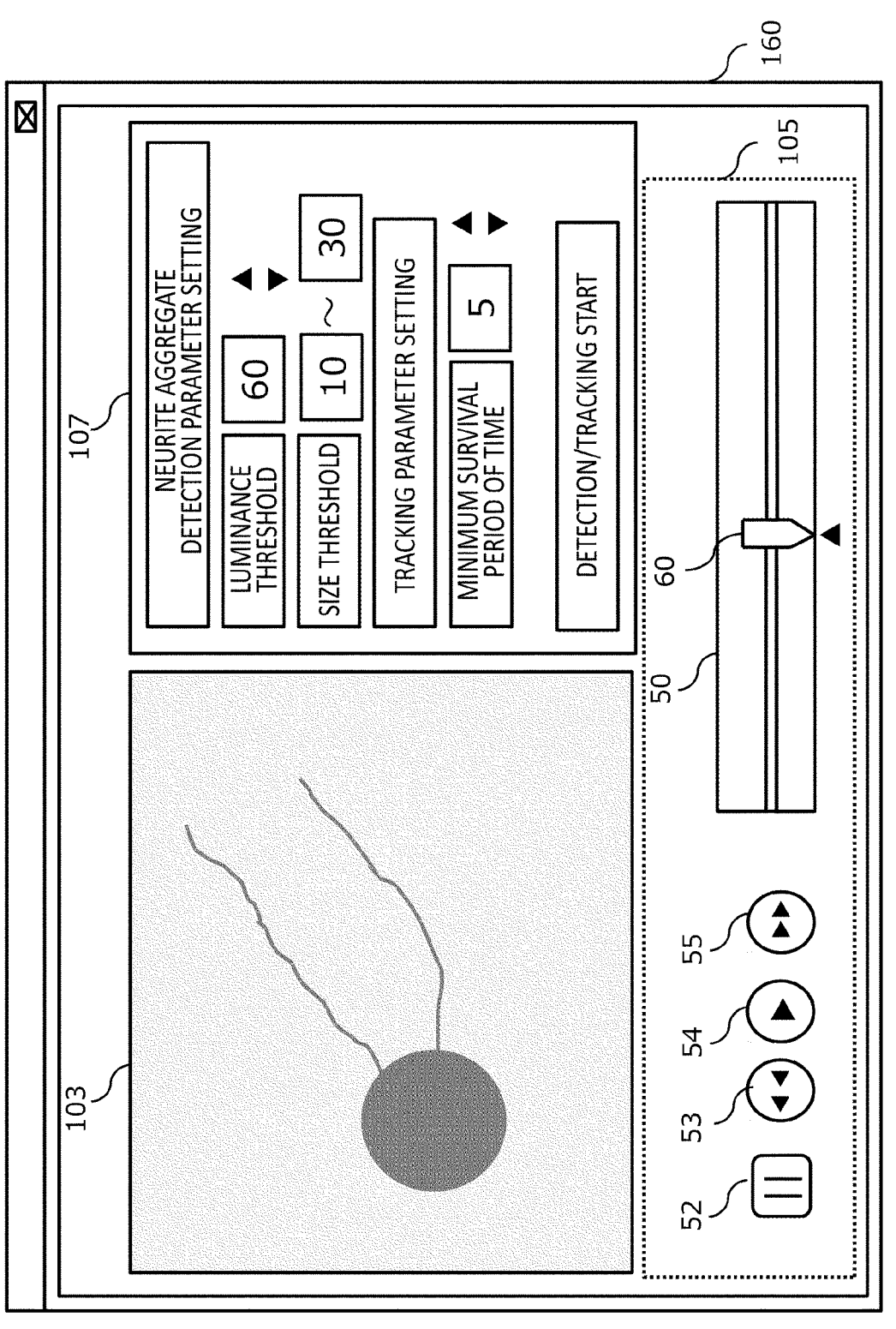
FIG. 7C illustrates an example of a screen displayed on the output unit of the device for analyzing neurons in the flow of detecting a neurite region in S250 in the present embodiment.

FIG. 7C is an example of a screen displayed in an enlarged view on the display region 103 by designating a predetermined region (may be referred to as a "region of interest (ROI)") from the captured image. In S252 and/or S254, the identification unit 350 may play back the acquired moving image file and display it on the display region 103. In addition, the identification unit 350 may enable the observer to select the ROI region to be displayed.

An appropriate luminance threshold and/or size threshold may be designated by the observer via the input unit 180. When the luminance threshold and/or the size threshold are designated by the observer, the display region 107 displays the designated luminance threshold and/or size threshold. These thresholds may be changeable by the observer arbitrarily inputting a numerical value in the numerical notation box of the display region 107. Next, the identification unit 350 may perform a series of processing of S252 to S255 on the basis of the designated luminance threshold and/or size threshold, and display the processed image on the display region 103. From the processed image displayed on the display region 103, a new luminance threshold and/or size threshold may be further designated by the observer. The luminance threshold and/or the size threshold may be designated by the observer any number of times until a desired image is obtained.

In the above example, a case has been described in which the neurite region is specified on the basis of the fluorescence derived from the first fluorescent protein, but the neurite region may be specified on the basis of the image obtained by phase difference observation in addition to/instead of the fluorescence.

After the identification unit 350 outputs, to the association unit 550 and the analysis unit 600, the image obtained by extracting the region exceeding the size threshold, the identification unit 350 allows the processing to proceed to S270.

Next, in S270, the identification unit 350 tracks the neurite. In S270, the step of tracking the neurite includes the steps of S271 to S275, as illustrated in FIG. 8A.

Figure 8A:
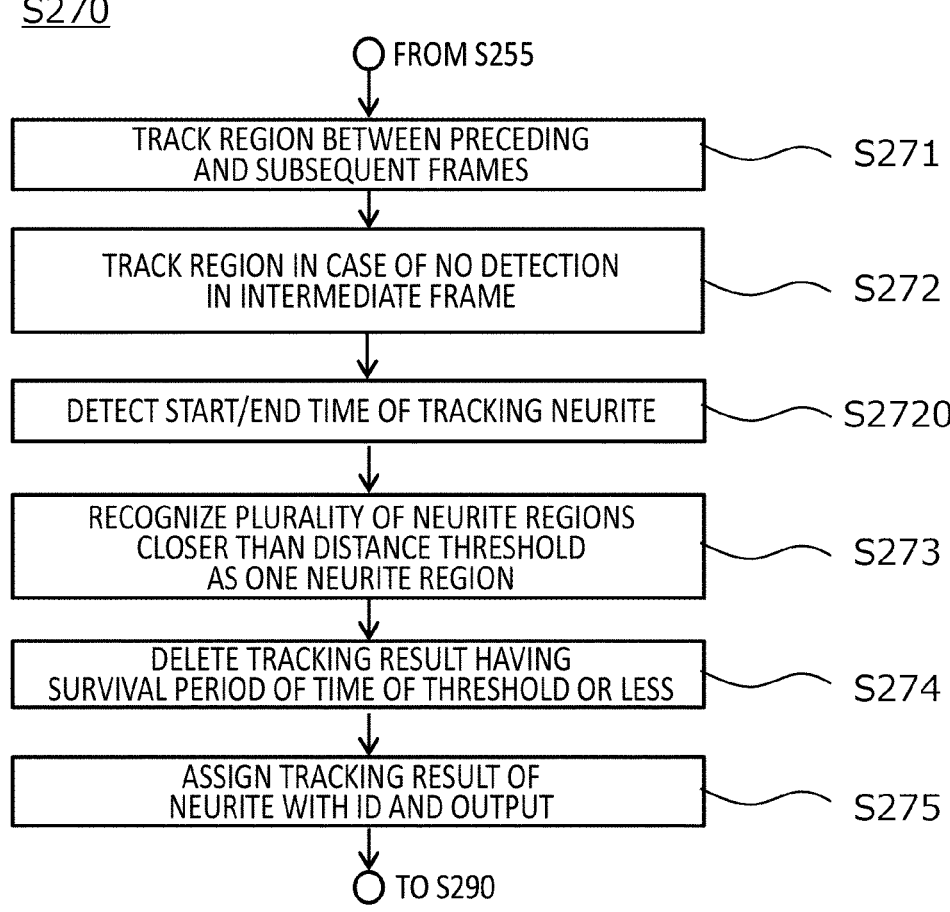
FIG. 8A illustrates an example of a flow for tracking a neurite in S270 in the present embodiment.

FIG. 8A illustrates S270 in the flow. First, in S271, the identification unit 350 tracks a region between preceding and subsequent frames for a plurality of time-series images.

Figure 8B:
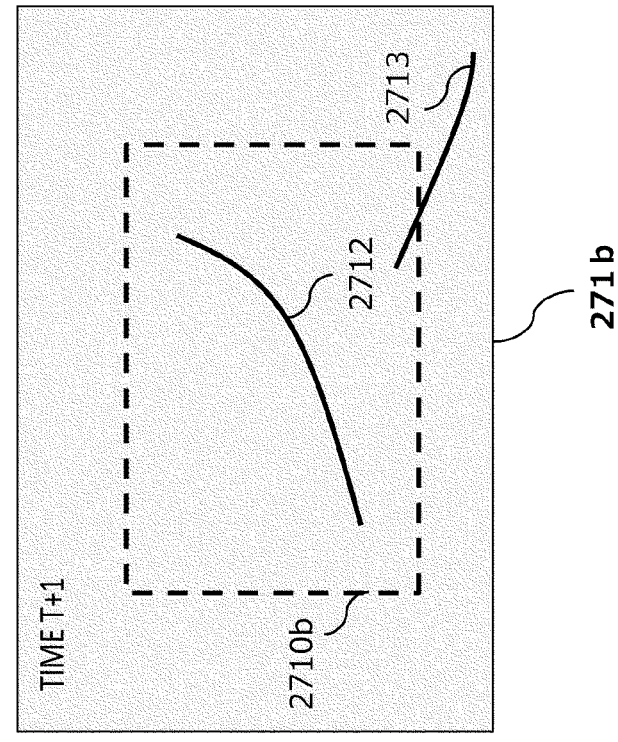
FIG. 8B illustrates an example of a flow of tracking a region between preceding and subsequent frames in S271 in the present embodiment.
Figure 8B:
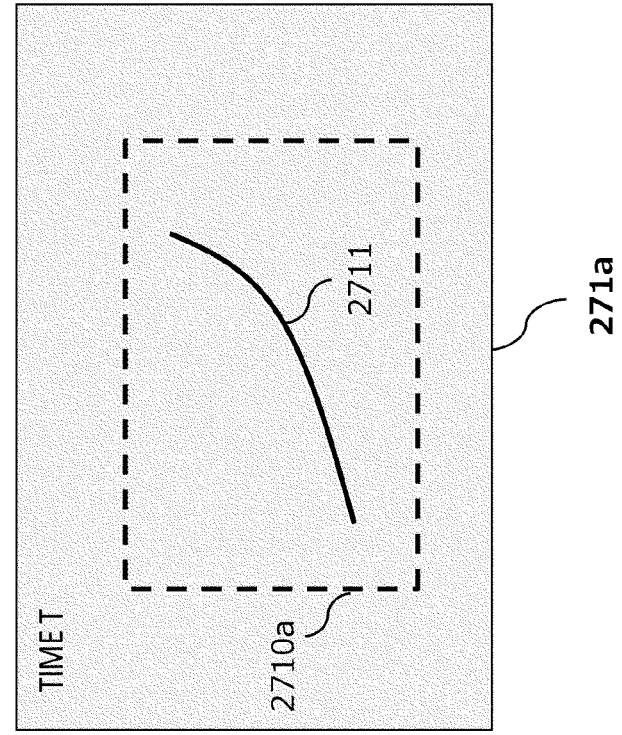

FIG. 8B is an example of tracking the region between preceding and subsequent frames for each connected region in the protrusion detection result (the image subjected to the series of processing of S252 to S255 and having been processed) image. For example, images used for neuron tracking processing may be an image 271*a* captured in the round of time T and including a cell region in the time-series images and an image 271*b* captured in the round of time T+1 immediately after time T and including a cell region in the time-series images. In the image 271*a*, the cell region is defined as 2711, and in the image 271*b*, the cell region is defined as a region 2712 and a region 2713. At this time, the identification unit 350 may set a search range 2710*a* around the region 2711 of the image 271*a*, set a search range 2710*b*, which is the region corresponding to the search range 2710*a*, in the image 271*b*, and search for whether there is the cell region in the search range 2710*b*. Here, a quadrangle circumscribing the cell region 2711 (for example, a rectangle) is considered as the search region 2710*a*, and a quadrangle in which the vertical and horizontal lengths are increased little by little (for example, 5%, 10%, 20%, or the like of the vertical and horizontal lengths) from the end point may be set as the search region. Furthermore, in addition to the quadrangle, any polygon, circle, or the like may be set as the search region.

For example, if there is a plurality of cell regions (for example, the region 2712 and the region 2713) in the search range 2710*b* of the image 271*b*, the identification unit 350 may recognize that the region 2712, which is a region having the largest overlap (a region having the largest overlap area) in the search range 2710*b*, is the same neurite and perform tracking. After the identification unit 350 tracks the region between the preceding and subsequent frames for all or some of the frames, the identification unit 350 allows the processing to proceed to S272.

Next, in S272, for the acquired time-series frames, the identification unit 350 tracks the cell region in a case where no neurite is detected in an intermediate frame. In the example of FIG. 8B, tracking is performed between two consecutive frames, but the preceding and subsequent frames for tracking are not limited to two consecutive frames, and tracking may be performed between frames of distant time points within a predetermined period of time. The identification unit 350 executes the processing of S271 and S272 for all rounds. For example, the identification unit 350 repeatedly executes the tracking from the first round (that is, T is 1) to the last round (that is, T is N which is the number of rounds for imaging).

For example, in imaging of neurons, the search region is set for the cell region of the image captured in the round of time T, but there may be a case where there is no corresponding cell region in the search region in the image captured in the round of time T+1. In this case, the identification unit 350 may further set, in the image captured in the round of time T+2 immediately thereafter, the search region around the region corresponding to the search region set in the round of time T, and track the cell region. That is, even if the corresponding cell region cannot be detected in the image captured in the round of time T+1, the search region may be set and searched in the image captured in the round of time T+2 immediately thereafter, and the cell region having the largest overlap with the search source region (the region having the largest overlap area) in the cell region may be recognized as the same neurite and tracked. After the identification unit 350 tracks the cell region of a case where no neurite is detected in the intermediate frame, the identification unit 350 allows the processing to proceed to S2720. A result of tracking for each neurite in to S272 is hereinafter also referred to as a "tracking result". Note that, in the above example, an example of tracking the cell region detected in the round of time T and the cell region in the image captured in the round of time 1+2 has been described, but the present invention is not limited to the round of time T+2, and for example, the cell region in the image captured in the round of time T+3, the time T+4, or the like may be tracked as the cell region detected in the round of time T.

Next, in S2720, the identification unit 350 detects the time of starting the tracking of the neurite and the time of ending the tracking. For example, for each neurite tracking result, the identification unit 350 may output, to the analysis unit 600, the time at which the tracking of each neurite has started and the tracking end time, save them in the recording unit 190, and/or output them to the output unit 160. Here, the tracking start time of the neurite may be the time of a frame, at which the neurite first emits fluorescence having luminance exceeding the threshold, in the captured image, and the tracking end time may be the time of a frame, at which the luminance of the neurite becomes equal to or less than the threshold, in the captured image. After the identification unit 350 detects the start and end times of the tracking of the neurite, the identification unit allows the processing to proceed to S273.

Next, in S273, the detection unit 400 recognizes, as one neurite region, a plurality of neurite regions closer than the distance threshold.

Figure 8C:
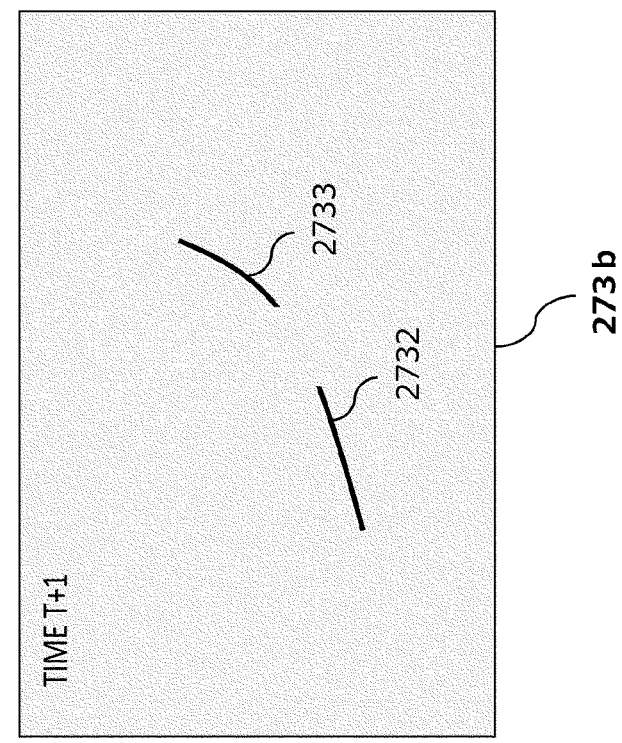
FIG. 8C is an example of a flow of recognizing, as one neurite region, a plurality of neurite regions closer than a distance threshold in S273 in the present embodiment.
Figure 8C:
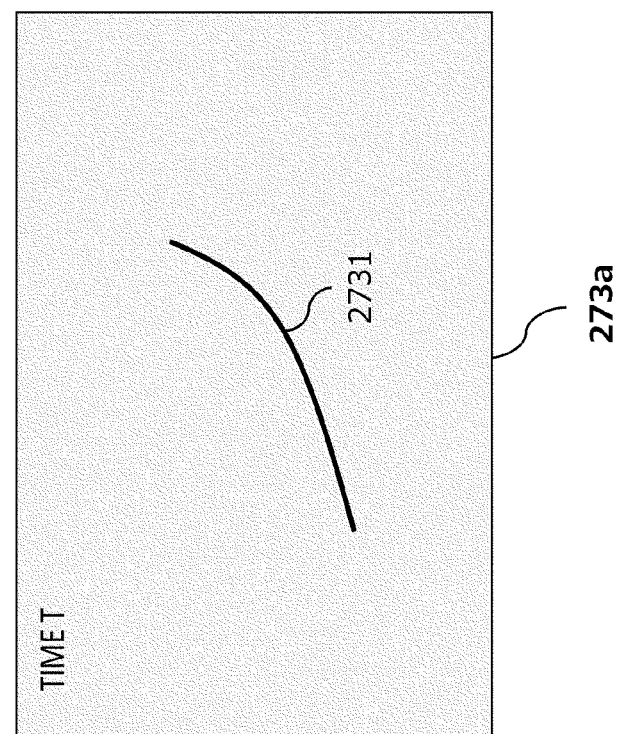

FIG. 8C is an example of recognizing, as one neurite region, a plurality of neurite regions closer than the distance threshold. The image captured in the round of time T is defined as an image 273*a*, and the image captured in the round of time T+1 immediately after time T is defined as 273*b*. In the image 273*a*, a cell region is defined as a region 2731, and in the image 273*b*, a cell region is defined as a region 2732 and a region 2733. As illustrated in FIG. 8C, the region 2731, the region 2732, and the region 2733 are considered to be obtained by imaging the fluorescence derived from the first fluorescent protein aggregated in the same neurite. However, in the image 273*b* captured in the round of time T+1, the neurite portion is disconnected to the region 2732 and the region 2733 due to imaging conditions or the like.

In such a case, even when the region 2732 and the region 2733 are disconnected, if the distance between the region 2732 and the region 2733 (for example, a distance between the end point of the region 2732 on a side close to the region 2733 and the end point of the region 2733 on a side close to the region 2732) is closer than a predetermined distance threshold, the detection unit 400 may recognize the neurites included in these regions (the region 2732 and the region 2733) as the same neurite, and assign the tracking result of the neurite with the same protrusion ID to be described later. By performing the step of S273, the neurite can be more accurately specified and tracked. Note that an appropriate value of the distance threshold may be designated by the observer via the input unit 180, or may be designated on the basis of a plurality of images acquired by the identification unit 350. In addition, the distance threshold may be the same as or different from the distance threshold in S232.

Furthermore, in addition to/instead of the distance threshold, the detection unit 400 may recognize neurites included in a plurality of regions as the same neurite by using, as an index, a direction of a straight line or a tangent line of the neurite included in the cell region. For example, when in the image 273b of FIG. 8C, the tangent line at the end point of the region 2732 on the side close to the region 2733 and the tangent line at the end point of the region 2733 on the side close to the region 2732 coincide with each other or have the same slope, the detection unit 400 may recognize the neurites included in these regions 2732 and 2733 as the same neurite. After the detection unit 400 recognizes that the plurality of neurite regions closer than the distance threshold are one neurite region, the detection unit 400 allows the processing to proceed to S274.

Next, in S274, the detection unit 400 deletes the tracking result of the neurite found to have the survival period of time equal to or less than the threshold as a result of the tracking in S272. In the case of a neuron having a neurite with a survival period of time equal to or less than the threshold among neurites in the cell region tracked by the detection unit 400, the detection unit 400 deletes the tracking result of the neurite. Here, the survival period of time may be a period of time between the time when the tracking of the neurite is started and the time when the tracking is ended.

For example, on the screen of FIG. 7C, the detection unit 400 may display, on the output unit 160, the display region 107 for inputting a threshold of the survival period of time, and request the observer to input the threshold of the survival period of time. An appropriate threshold of the survival period of time may be designated by the observer via the input unit 180. On the basis of the designated threshold of the survival period of time, the detection unit 400 may delete the tracking result of the neurite having the survival period of time equal to or less than the threshold. After the detection unit 400 deletes the tracking result of the neurite having the survival period of time equal to or less than the threshold, the detection unit 400 allows the processing to proceed to S275.

Next, in S275, the detection unit 400 assigns an ID to the tracking result of the neurite in the image acquired in S255 and outputs the result. The detection unit 400 assigns a unique ID (neurite ID) to the tracking result of each neurite tracked between the acquired time-series frames. That is, the neurites assigned with the same neurite ID represent the same neurite.

For example, in FIG. 8B, the detection unit 400 may regard the regions 2711 and 52712 as regions having the same neurite and assign the same neurite ID thereto. The detection unit 400 outputs the neurite ID together with the image to the association unit 550. In addition, the detection unit 400 may save the neurite ID in the recording unit 190 and/or output it to the output unit 160.

By performing all or some of the steps of S251 to S275 described above and associating the neurite with the cell body as described later, the detection unit 400 may determine that the cell having the neurite exceeding the luminance threshold and the size threshold is a neuron in which aggregates exist inside the neurite. In this case, the detection unit 400 determines that the cell region from which the neurite has been extracted is a region where the aggregates exist. In the above example, the detection unit 400 extracts the cell region exceeding the luminance threshold and the size threshold, but the detection unit 400 may extract the cell region by using only the luminance threshold. In this manner, the detection unit 400 can detect the presence or absence of aggregates existing inside the neurite. The steps of S273 to S275 performed by the detection unit 400 may be referred to as a first aggregate detection process (step), that is, a step of detecting the aggregates existing inside the neurite. The "first aggregate detection process" and a "second aggregate detection process" may be simply referred to as an "aggregate detection process".

In addition, in the above example, a case has been described in which the luminance threshold is set to determine the presence or absence of aggregates (intra-cell body aggregates) existing inside the cell body and aggregates (intra-neurite aggregates) existing inside the neurite, but the luminance threshold may include the average value (m) and/or variance value (σ) of the luminance. For example, the detection unit 400 may calculate the average value (m) and variance value (σ) of luminance of the cell body region and/or the neurite region in each time-series image, and determine a region having luminance of m+σ, m+2σ, or m+3σ or more as a region where aggregates exists.

In addition, in the above example, a case has been described in which only the first fluorescent protein is expressed as the fluorescent protein in the neuron, but for example, in addition to the first fluorescent protein, second fluorescent protein different from the first fluorescent protein may be further expressed in the neuron, and all or some steps from S200 to S275 may be performed on the second fluorescent protein in addition to the first fluorescent protein. Here, the second fluorescent protein may be obtained by adding a fluorescent tag to protein exhibiting aggregation propensity in a neuron (neurite and/or cell body), or may be protein not exhibiting aggregation propensity in a neuron. The fluorescent tag of the second fluorescent protein is preferably different in fluorescent wavelength (color tone) from the fluorescent tag of the first fluorescent protein for convenience of observation and analysis. For example, when the fluorescent tag of the first fluorescent protein is GFP (green), the fluorescent tag of the second fluorescent protein may be RFP (red).

For example, the second fluorescent protein may be a fluorescent tag protein itself such as GFP or RFP. It is known that GFP or RFP itself is universally expressed in cell bodies and neurites when introduced into neurons. Therefore, by expressing the fluorescent tag protein itself such as GFP or RFP as the second fluorescent protein in the neuron, it can be easily determined that the neuron is dead, for example, if a state where the fluorescence luminance emitted by the fluorescent tag protein is less than the luminance threshold continues for a predetermined period of time or more.

For example, the second fluorescent protein may be obtained by adding a fluorescent tag to marker protein localized in axons of neurons or marker protein localized in dendrites. The "localization" may be a concept included in "aggregation". In the culturing of neurons, neurites of a large number of neurons overlap each other, and thus it is difficult to distinguish axons and dendrites for observation. Therefore, in the above example, axons and dendrites are treated as neurites without distinction. In this regard, by expressing the second fluorescent protein obtained by adding a fluorescent tag to axon marker protein or dendrite marker protein in addition to the first fluorescent protein exhibiting aggregation propensity in neurons, it is possible to clearly determine whether intra-neurite aggregates exist inside axons or whether intra-neurite aggregates exist inside dendrites. Examples of the axon marker protein include synapsin 1 protein and synaptophysin protein, and examples of the dendrite marker protein include PSD-95 protein. The following steps of S290 and S310 may be performed on the second fluorescent protein in addition to the first fluorescent protein.

In S290, the association unit 550 specifies association between the neurite and the cell body on the basis of the neurite ID and the cell body ID acquired from the identification unit 350 and a plurality of images.

Figure 9:
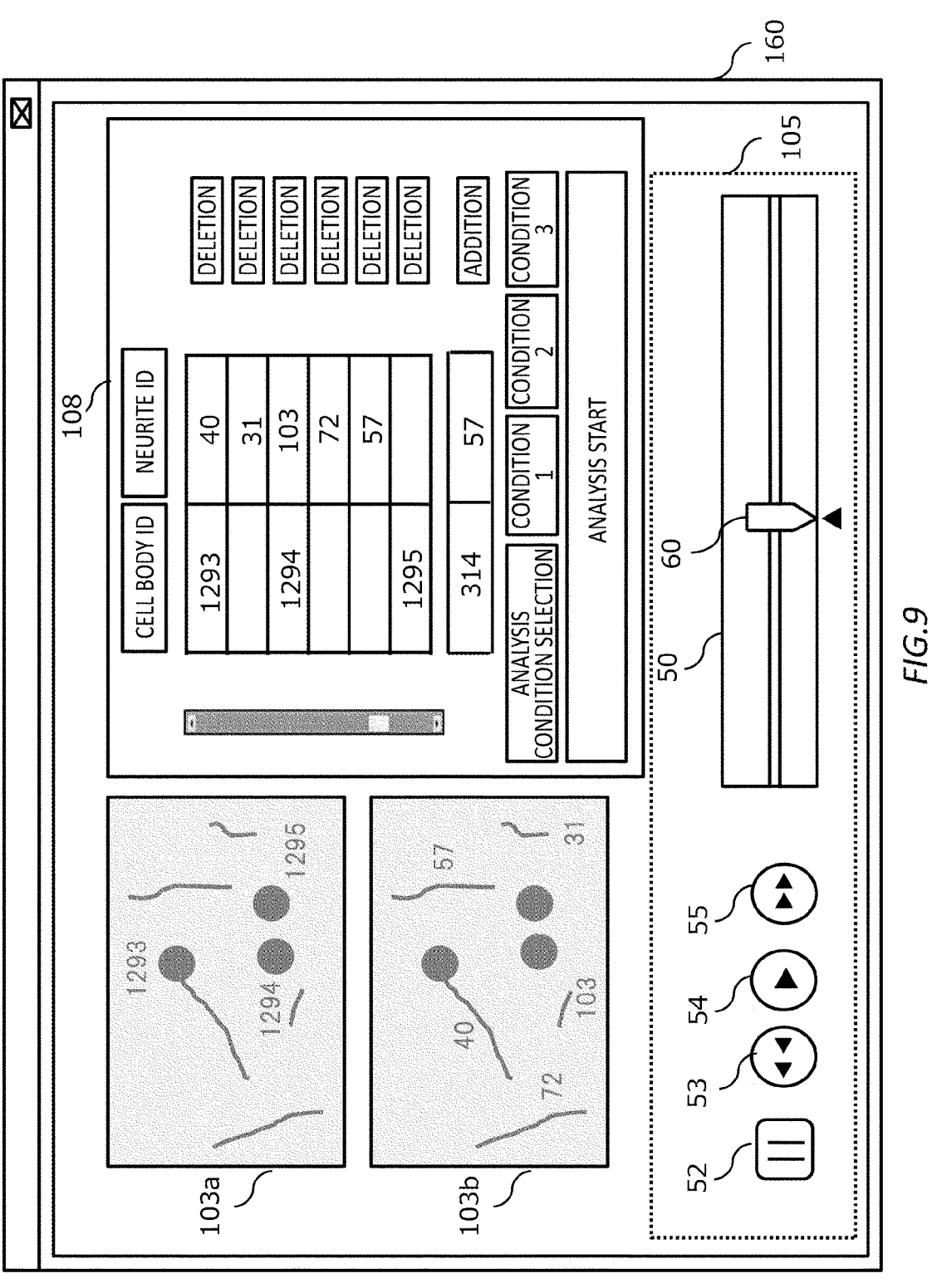
FIG. 9 illustrates an example of a screen displayed on the output unit of the device for analyzing neurons in a flow of associating neurites with cell bodies in S290 in the present embodiment.

FIG. 9 is an example of a screen displayed on the output unit 160 of the device for analyzing neurons in S290. The association unit 550 may output the screen illustrated in FIG. 9 to the output unit 160. An image assigned with a cell body ID is displayed on the display region 103a, and an image assigned with a neurite ID is displayed on the display region 103b. Here, the image displayed on the display region 103a and the image displayed on the display region 103b may be the image transmitted from the imaging device control unit 171 and acquired in S206, or may be the images output in the steps of S215 and S255, respectively.

In the display region 108, some candidates for association between the cell body ID and the neurite ID are displayed. The association unit 550 associates the cell body ID "1293" with the neurite ID "40", and determines the cell body ID "1294" and the neurite ID "103" as a candidate for association. The association unit 550 may extract candidates for association between the cell body ID and the neurite ID on the basis of a distance between the cell body region and the neurite region, and the association unit 550 may display the candidates on the display region 108 in descending order of a probability of having a corresponding relationship. For example, the association unit 550 may determine that the closer the distance between the cell body region and the neurite region, the higher the probability of the corresponding relationship. Furthermore, in addition to/instead of the distance between the cell body region and the neurite region, the association unit 550 may determine that the cell body region in an extension direction of the tangent line at the end point of the neurite in the neurite region has a high probability of having the corresponding relationship.

An appropriate association may be selected by the observer from among the candidates for association between the cell body ID and the neurite ID described above. As a result of the observer viewing the displayed screen, via the input unit 180, the observer may delete an inappropriate candidate for association by a "delete" button and an "add" button in FIG. 9 and add an association considered to be appropriate in order to select an appropriate association. The appropriate association may be performed only by the association unit 550 or may be performed only by designation of the observer.

In addition, the analysis unit 600 may classify a cell group, in which the cell body ID and the neurite ID can be associated with each other and in which aggregates exist in the cell body, among the neurons, into a "cell group in which intra-cell body aggregates and intra-neurite aggregates exist". The analysis unit 600 may classify a cell group, which is assigned with the cell body ID but not assigned with the corresponding neurite ID and in which aggregates exist in the cell body, among the neurons, into a "cell group in which intra-cell body aggregates exist but no intra-neurite aggregate exists". The analysis unit 600 may classify a cell group, in which the cell body ID and the neurite ID can be associated with each other and in which no aggregate exists in the cell body, among the neurons, into a "cell group in which intra-neurite aggregates exist but no intra-cell body aggregate exist". The analysis unit 600 may classify a cell group, which is assigned with the cell body ID but not assigned with the corresponding neurite ID and in which no aggregate exists in the cell body, among the neurons, into a "cell group in which no intra-cell body aggregate and no intra-neurite aggregate exists". The analysis unit 600 performs the above four classifications and performs various types of analysis to be described below.

After the appropriate association between the cell body ID and the protrusion ID is performed by the association unit 550, the analysis unit 600 performs the four classifications as described above, and allows the processing to proceed to S310.

Next, in S310, the analysis unit 600 acquires the association between the cell body ID and the neurite ID from the association unit 550, and analyzes the survival period of time of the associated neuron. For example, the analysis unit 600 may analyze and calculate a survival/death ratio and/or a survival period of time for each of neurons having intra-neurite aggregates and neurons not having intra-neurite aggregates. Here, regarding the survival or death of the cell, if the luminance of the neurite or the cell body is less than the luminance threshold, the neuron may be defined as dead. Note that the step of S310 may be referred to as an "analysis process".

For example, for the cell group classified into a "cell group in which intra-cell body aggregates exist but no intra-neurite aggregate exists", in a state where a cell body is no longer detected in the middle of the imaged frame, that is, if the tracking end time is recorded in S2320, the analysis unit 600 may determine that the cell having the cell body is dead. In addition, if a cell body emits fluorescence with luminance exceeding the threshold up to the last frame in the image, that is, if the tracking end time is not recorded in S2320, the identification unit 350 may determine that the cell having the cell body is alive.

For example, the calculation of the survival/death ratio or the survival period of time of neurons may be performed as follows. The analysis unit 600 may calculate the number of cell body IDs determined to be alive and the number of cell body IDs determined to be dead, and calculate, as the survival/death ratio, a value obtained by dividing the number of cell body IDs determined to be alive by the sum of the number of cell body IDs determined to be alive and the number of cell body IDs determined to be dead. In addition, the analysis unit 600 may calculate, as the survival period of time, a period of time between the earliest time and the latest time of frames in which a cell body are consecutively detected.

For example, in the cell group classified into a "cell group in which intra-neurite aggregates exist but no intra-cell body aggregate exists", for the cell body region in which intra-neurite aggregates exist and which has the cell body ID corresponding to the neurite ID, the analysis unit 600 may determine the survival or death of the cell group, in which intra-neurite aggregates exist, on the basis of whether the tracking end time is recorded in S2320. Alternatively, if the second fluorescent protein is expressed in the neuron, for the cell group in which intra-neurite aggregates exist, the analysis unit 600 may determine the survival or death of the cell group, in which intra-neurite aggregates exist, by using, as an index, the fluorescence luminance emitted by the second fluorescent protein. As an example, if a state where the luminance emitted by the second fluorescent protein is less than the luminance threshold continues until the end of imaging, it may be determined that the cell group in which intra-neurite aggregates exist is dead.

For the survival or death of the cell group classified into the "cell group in which intra-cell body aggregates and intra-neurite aggregates exist", the analysis unit 600 may make determination similar to the determination for the cell group in which intra-cell body aggregates exist but no intra-neurite aggregate exists, or may make determination similar to the determination for the cell group in which intra-neurite aggregates exist but no intra-cell body aggregate exists. The analysis unit 600 may determine that at the time when a cell body is no longer detected (that is, the tracking end time of the cell body) in the middle of the imaged frame, the cell having the cell body is dead. If the time when the cell body is no longer detected is different from the time when neurites are no longer detected, the analysis unit 600 may determine that the earlier time is the time when the cell is dead, or may determine that the later time is the time when the cell is dead.

For the cell group classified into the "cell group in which no intra-cell body aggregate and no intra-neurite aggregate exists", similarly to other groups, in a state where a cell body is no longer detected in the middle of the imaged frame, that is, if the tracking end time is recorded in S2320, the analysis unit 600 may determine that the cell having the cell body is dead.

For example, the analysis unit 600 may analyze and calculate a survival/death ratio and/or a survival period of time for each of neurons having intra-cell body aggregates and neurons not having intra-cell body aggregates. For example, the analysis unit 600 may analyze and calculate a survival/death ratio and/or a survival period of time for each of the "four cell groups divided by the presence or absence of intra-neurite aggregates and the presence or absence of intra-cell body aggregates" described above.

These analysis conditions may be set in the analysis unit 600 in advance, and in this case, the analysis unit 600 may output the analysis conditions to the output unit 160 to be able to be designated by the observer via the input unit 180 in the display region 108 of FIG. 9. For example, when condition 1 is selected by the observer in the display region 108 of FIG. 9, the analysis unit 600 may receive the input and analyze and calculate the survival period of time of each of neurons in which intra-neurite aggregates exist and neurons in which no intra-neurite aggregate exist. For example, when condition 2 is selected by the observer in the display region 108 of FIG. 9, the analysis unit 600 may receive the input and analyze and calculate the survival period of time of each of the four cell groups divided by the presence or absence of intra-neurite aggregates and the presence or absence of intra-cell body aggregates.

Figure 10A:
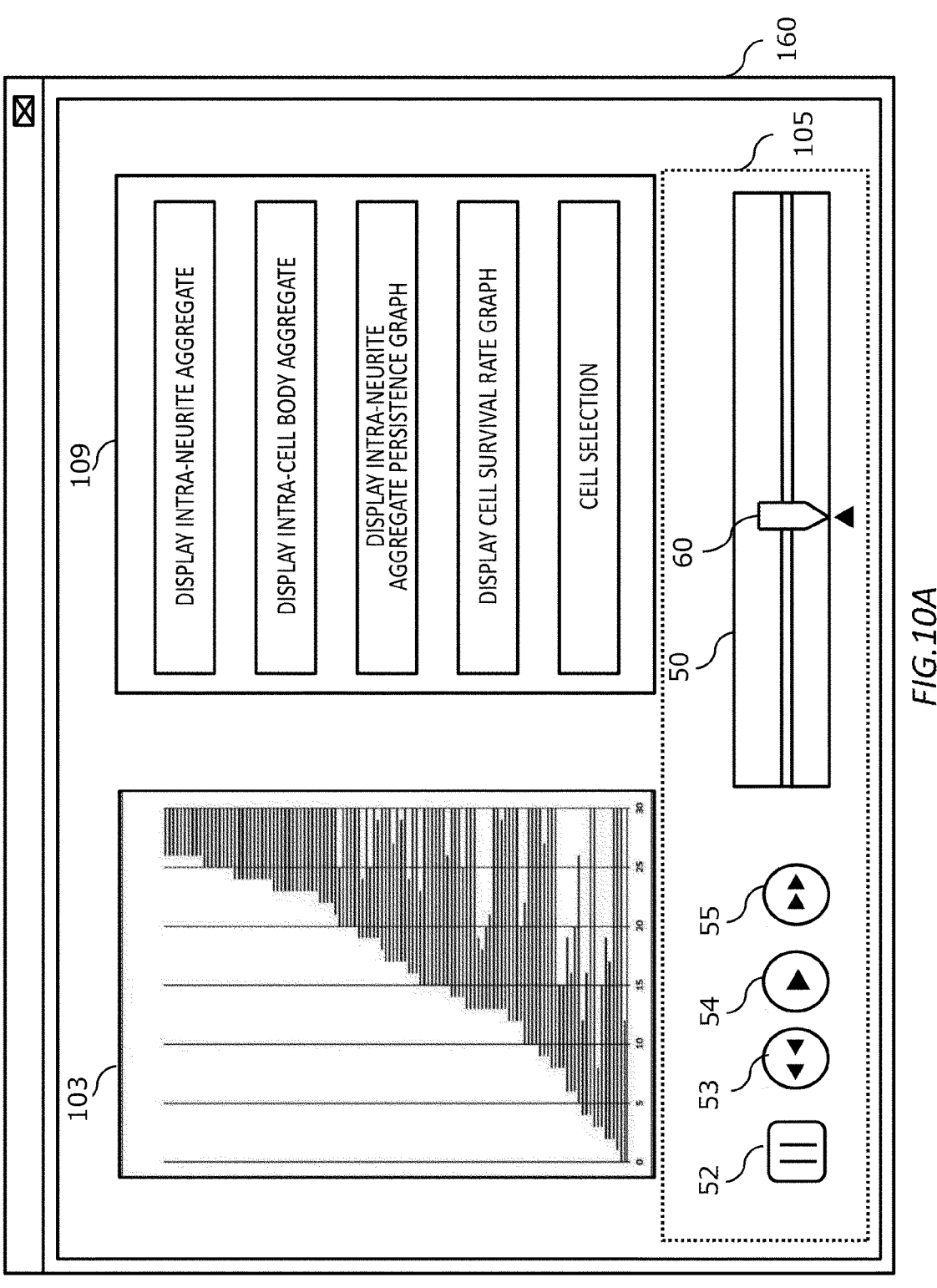
FIG. 10A illustrates an example of a screen displayed on the output unit of the device for analyzing neurons in a flow of analyzing a survival period of time of a neuron in S310 in the present embodiment.

FIG. 10A is an example of a screen displayed on the output unit 160 in S310. The analysis unit 600 may display the analysis result in the display region 103. For example, if "display intra-neurite aggregate" of the display region 109 is selected by the observer, the analysis unit 600 may display, on the display region 103, an image in which a time-series fluorescence image or phase difference image is superimposed with what intra-neurite aggregates are masked. For example, if "display intra-cell body aggregate" of the display region 109 is selected by the observer, the analysis unit 600 may display, on the display region 103, an image in which a time-series fluorescence image or phase difference image is superimposed with what intra-cell body aggregates are masked.

In addition, if "cell selection" in the display region 109 is selected by the observer, the analysis unit 600 may display, on the display region 103, an image or a moving image of only the periphery of a selected cell or analysis data of the selected cell. For example, the analysis data of the cell may be data such as a ratio of the area of aggregates in a cell body to the cell body, the area of intra-neurite aggregates, or the period of time during which the intra-neurite aggregates exist. Here, the area of the intra-neurite aggregate may be the sum of all pixels included in the region where the intra-neurite aggregates exist, and the area may be represented by a square pixel or a value obtained by conversion into a square micrometer.

For example, if "display intra-neurite aggregate persistence graph" in the display region 109 is selected by the observer, the analysis unit 600 may graph, for each neurite ID, when intra-neurite aggregates appear and when the intra-neurite aggregates disappear in the time-series images and display the result on the display region 103.

Figure 10B:
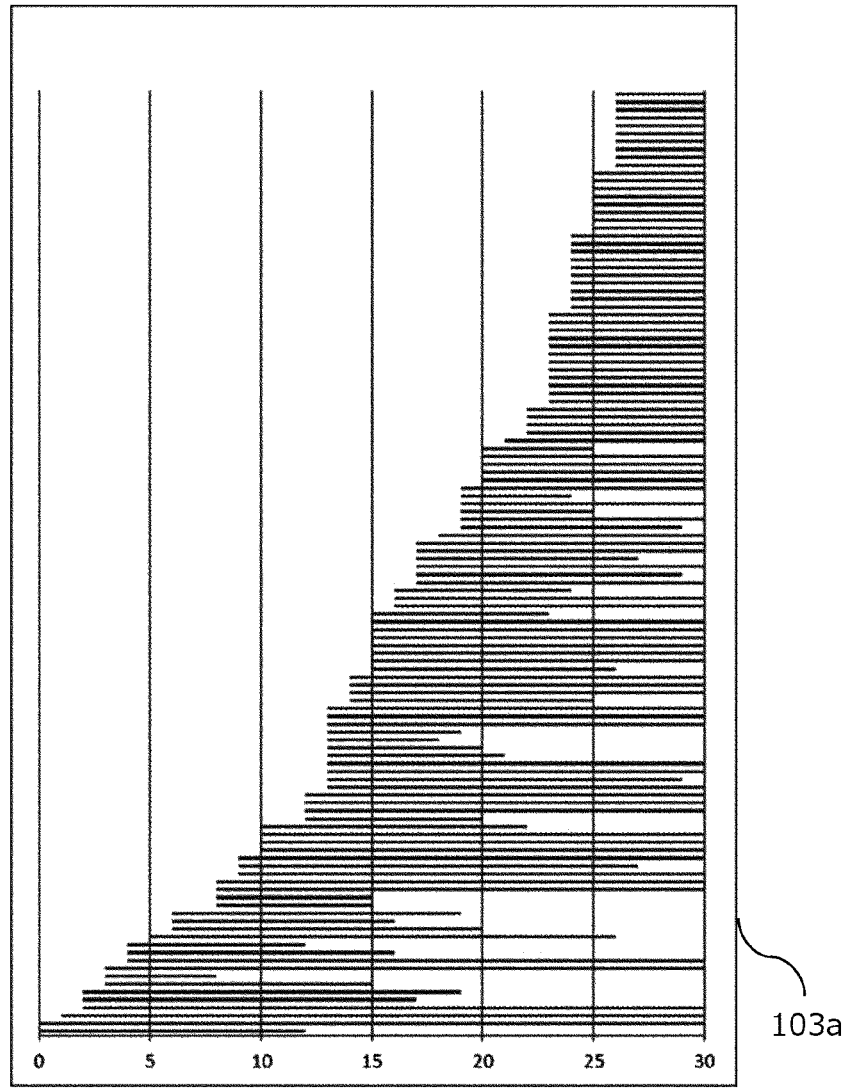
FIG. 10B illustrates an example of an intra-neurite aggregate persistence graph displayed on the output unit of the device for analyzing neurons in the flow of analyzing a survival period of time of a neuron in S310 according to the present embodiment.

FIG. 10B is an example of an intra-neurite aggregate persistence graph to be displayed on the output unit 160. In an intra-neurite aggregate persistence graph 103a of FIG. 10B, a vertical axis represents the neurite ID, and a horizontal axis represents a period of time, during which the intra-neurite aggregates exist in the region of each neurite ID, with the frame number of the time-lapse imaging. The straight line extending in the horizontal direction of the graph indicates the period of time during which the intra-neurite aggregates exist. Here, the left end of the straight line of the graph may be the time when the intra-neurite aggregates are detected for the first time, and the right end of the straight line of the graph may be the time when the intra-neurite aggregates are no longer detected or the time when it is determined that the cell is dead. For example, when the straight line in the graph is clicked by the observer, the analysis unit 600 may display, on the output unit 160, the moving image of the frame in which the intra-neurite aggregates corresponding to the neurite ID exist. In addition, when the straight line in the graph is clicked by the observer, the analysis unit 600 may display the persistence graph of the intra-cell body aggregates of the cell body ID corresponding to the neurite ID side by side. Furthermore, the analysis unit 600 may divide cell groups by the presence or absence of intra-cell body aggregates and display an intra-neurite aggregate persistence graph for each cell group.

In addition, if "cell survival rate graph" of the display region 109 is selected by the observer, the analysis unit 600 may calculate the survival rate of neurons for each time in the time-series images, graph the survival rate, and display the result on the display region 103.

Figure 10C:
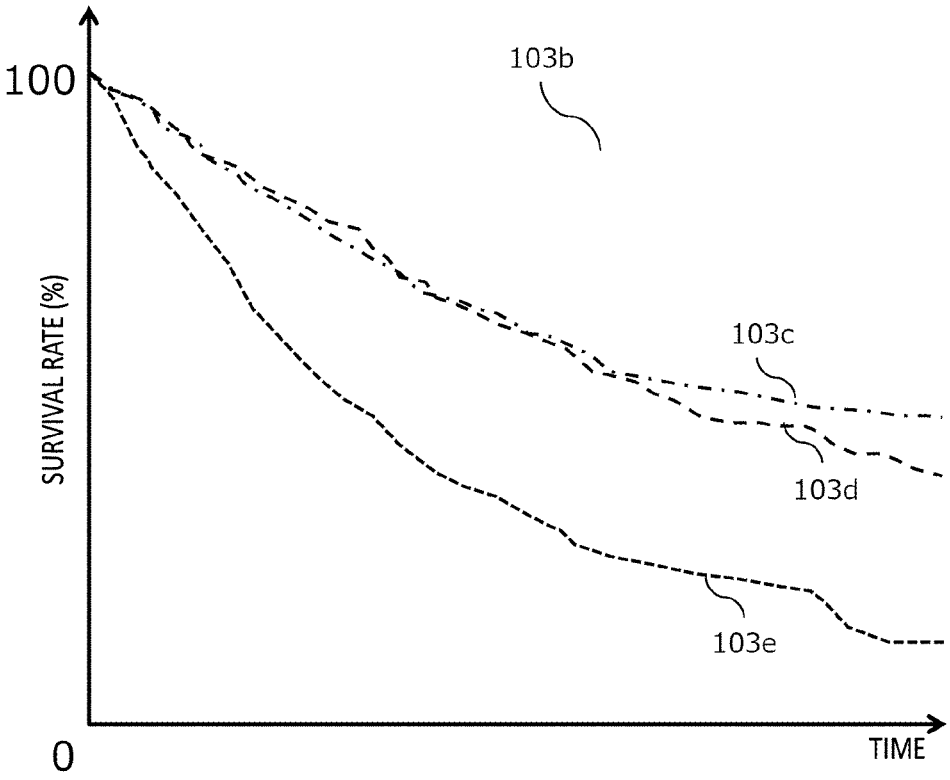
FIG. 10C illustrates an example of a cell survival rate graph displayed on the output unit of the device for analyzing neurons in the flow of analyzing a survival period of time of a neuron in S310 in the present embodiment.

FIG. 10C is an example of a cell survival rate graph to be displayed on the output unit 160 of the device for analyzing neurons 1. In a cell survival rate graph 103b of FIG. 10C, a horizontal axis represents time, a vertical axis represents the survival rate, and the survival rate of the cell group at the start time is converted into 100% to be displayed. For example, a curve 103c may be the survival rate curve of the cell group in which intra-cell body aggregates exist but no intra-neurite aggregate exist, a curve 103d may be the survival rate curve of the cell group in which intra-neurite aggregates exist but no intra-cell body aggregate exists, and a curve 103e may be the survival rate curve of the cell group in which both intra-cell body aggregates and intra-neurite aggregates exist. For each of the classified cell groups, the analysis unit 600 counts how many cells survive in each captured frame, and calculates a value obtained by dividing the result by the number of surviving cells counted in the first frame for each frame, thereby calculating the survival rate curve.

In FIG. 10C, the analysis unit 600 may display, on the output unit 160, the coordinates of an intersection of the plurality of graphs, that is, the time when the survival rate of the cell group is reversed and the survival rate at the time. In addition, in FIG. 10C, the analysis unit 600 may display, on the output unit 160, the coordinates of a point at which the slope of the curve at a certain time greatly changes. At a certain time, the time when the gradient of the slope becomes steeply large indicates the time when a large number of cells die at once. In addition, the time when the gradient of the slope becomes horizontal indicates the time when the survival rate of the cell becomes constant. The analysis unit 600 displays the coordinates of these points on the output unit 160, so that it becomes easy to perform dynamic analysis of neurons.

FIG. 10C illustrates an example of the survival rate curves for the cell groups divided by the presence or absence of intra-neurite aggregates and the presence or absence of intra-cell body aggregates, but the grouping of the cell group is not limited thereto. For example, the analysis unit 600 may perform grouping into a cell group in which aggregates exist from the imaging start time point, a cell group in which aggregates appear from the middle of the period of time of imaging, and a cell group in which no aggregate exist within the period of time of imaging, and display each of the survival rate curves of these cell groups on the output unit 160.

In addition, for example, the analysis unit 600 may perform grouping into a cell group having a relatively large number of aggregates (alternatively, a large number of cell regions) and a cell group having a relatively small number of aggregates (alternatively, a small number of cell regions), and display each of the survival rate curves of these cell groups on the output unit 160. In addition, for example, the analysis unit 600 may perform grouping into a cell group having aggregates on the side of the neurite close to the cell body and a cell group having aggregates on the side of the neurite close to the terminal, and display each of the survival rate curves of these cell groups on the output unit 160.

In addition to the above examples, the analysis unit 600 may display, as a time-lapse image, the behavior of the intra-neurite aggregate on the output unit 160. For example, α-synuclein protein is known to localize at an axon terminal in a physiological state. The analysis unit 600 displays, on the output unit 160, an aspect in which the aggregates of α-synuclein protein move from the terminal side to the cell body side in a neurite, when the movement is started, or the like, thereby facilitating dynamic analysis of neurons.

As described above, by using the device for analyzing neurons 1 of the present invention, for example, a small interfering RNA (siRNA) thereof, or the like) are administered to neurons, whether aggregates are formed inside neurites and/or a cell body, whether the aggregates move, or whether there is a change in the survival rate of neurons can be analyzed easily after various drug candidates (for example, a compound, protein or mutant protein thereof.

Next, a modified example of the present embodiment is shown. Neurons may be analyzed by combining a plurality of modified examples described below.

First Modified Example

Figure 11:
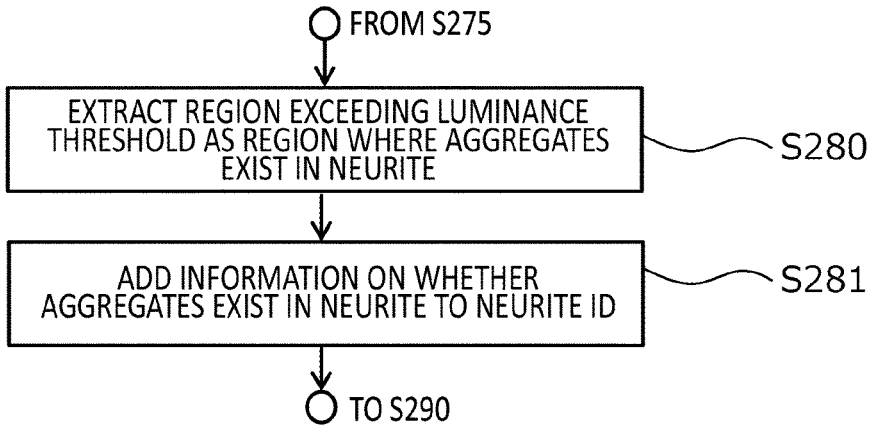
FIG. 11 illustrates flows of S280 and S281 of a first modified example.

FIG. 11 is a modified example of determining aggregates in a neurite region. In the present embodiment described with reference to FIG. 8A or the like, the detection unit 400 extracts a region exceeding the luminance threshold and the size threshold and recognizes (identifies) the region as the neurite region, and further determines the region as a region where aggregates exist in the neurite (may be referred to as an "intra-neurite aggregate region"). In the first modified example, the processing proceeds to S280 before the detection unit 400 proceeds to S290 after S275.

In S280, the detection unit 400 recognizes, as the neurite region, the cell region extracted in the steps of S271 to S275. Next, by using a luminance threshold different from the luminance threshold used in the step of S252, the identification unit 350 may determine that the region exceeding the luminance threshold is the intra-neurite aggregate region and extract the region. Specifically, the luminance threshold for extracting the intra-neurite aggregate region used in S280 may be larger than the luminance threshold for extracting the neurite region used in S252. After the step of S280, the detection unit 400 allows the processing to proceed to S281.

In S281, the detection unit 400 adds, to the neurite ID assigned in S275, information as to whether the intra-neurite aggregate region exists. Specifically, the detection unit 400 adds information, which indicates that the intra-neurite aggregate region exists, to the neurite ID of the neurite where the aggregates extracted in S280 exist. The detection unit 400 may output, to the analysis unit 600, the neurite ID to which the information indicating that the intra-neurite aggregate region exists is added. As described above, the intra-neurite aggregate region is specified by using the luminance threshold different from the luminance threshold for extracting the neurite region used in S252, so that it is possible to analyze the position where aggregates exist in the neurite region in each frame (for example, whether the aggregates are on the cell body side or terminal side of the neurite), and thus, it is possible to perform more detailed analysis.

Second Modified Example

In the present embodiment, the identification unit 350 determines that a region having a larger luminance among regions from which cell bodies have been extracted is a region where aggregates exist (intra-cell body aggregate region). In the second modified example, the identification unit 350 may determine that a cell having a cell region at a predetermined ratio (for example, a ratio of the area of the cell region to the area of the entire cell body, or the like) is a cell having the intra-cell body aggregate region. Here, the "intra-neurite aggregate region" and the "intra-cell body aggregate region" may be simply referred to as an "aggregate region".

Specifically, after the detection unit 400 finishes the step of S235, the detection unit 400 calculates each of the areas of the cell body region and the cell region. Here, the area of the entire cell body and the area of the cell region may be the sum of all pixels included in the region from which the cell body has been extracted and the sum of all pixels included in the cell region, and the area may be represented by a square pixel or a value obtained by conversion into a square micrometer. Next, the detection unit 400 may calculate a value obtained by dividing the area of the cell region by the area of the cell body region. The detection unit 400 may determine that a cell of which a ratio of the area of the cell region to the area of the entire cell body is a predetermined value or more is a cell having the intra-cell body aggregate region. The predetermined value may be 3%, 5%, or 10%, but is not limited thereto.

In addition, if the second fluorescent protein is further expressed in the neuron as described above, the detection unit 400 may determine that a region where the second fluorescent protein has luminance equal to or higher than the threshold is a cell body region and calculate the area of the cell body region. Next, after calculating the area of the cell region as described above, a value obtained by dividing the area of the cell region by the area of the cell body region may be calculated.

Figure 12:
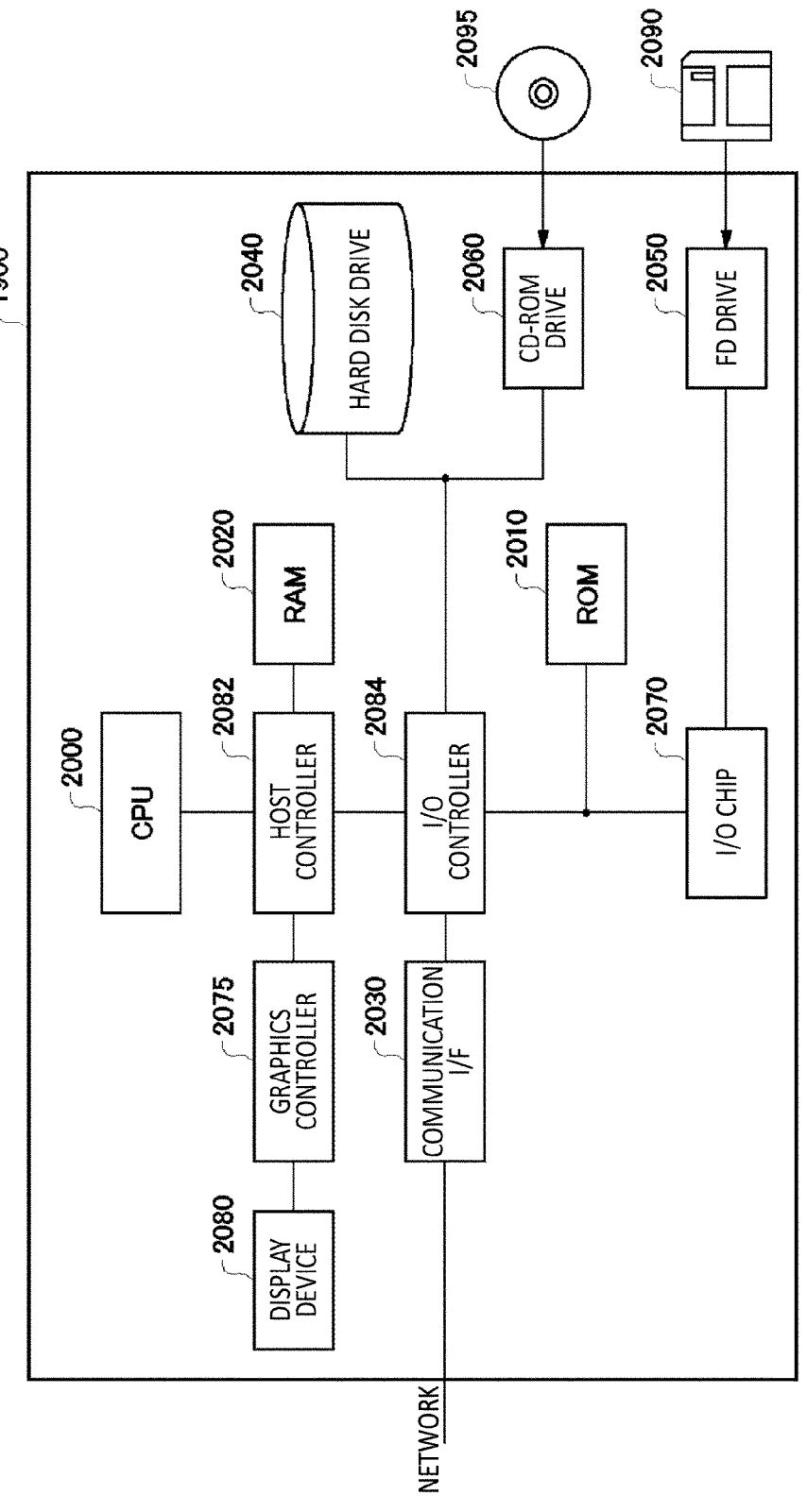
FIG. 12 illustrates an example of a hardware configuration of a computer.

FIG. 12 illustrates an example of a hardware configuration of a computer 1900 which functions as the arithmetic device 170. The computer 1900 according to the present embodiment includes: a CPU-peripheral portion having a CPU 2000, a RAM 2020, a graphics controller 2075, and a display device 2080 interconnected by a host controller 2082; and an input/output unit having communication interface 2030, a hard disk drive 2040, and a CD-ROM drive 2060 connected to the host controller 2082 by an input/output controller 2084; and a legacy input/output unit having a ROM 2010, a flexible disk drive 2050, and an input/output chip 2070 connected to the input/output controller 2084.

The host controller 2082 connects the RAM 2020 with the CPU 2000 and the graphics controller 2075 accessing the RAM 2020 at a high transfer rate. The CPU 2000 operates on the basis of programs stored in the ROM 2010 and the RAM 2020, and controls each unit. The graphics controller 2075 is configured to acquire image data generated by the CPU 2000 or the like on a frame buffer provided inside the RAM 2020 and display the image data on the display device 2080. Alternatively, the graphics controller 2075 may include therein a frame buffer storing the image data generated by the CPU 2000 or the like. The display device 2080 can display various types of information (for example, a moving image, an analysis result, and the like) generated inside the arithmetic device 170.

The input/output controller 2084 connects the communication interface 2030, the hard disk drive 2040, and the CD-ROM drive 2060 which are relatively fast input/output devices to the host controller 2082. The communication interface 2030 is configured to communicate with other devices via a network by wire or wirelessly. In addition, the communication interface is configured to function as a hardware to perform communications. The hard disk drive 2040 stores a program and data to be used by the CPU 2000 in the computer 1900. The CD-ROM drive 2060 is configured to read a program or data from the CD-ROM 2095 and provide the hard disk drive 2040 via the RAM 2020.

In addition, the ROM 2010, and the flexible disk drive 2050 and input/output chip 2070, which are relatively low-speed input/output devices, are connected to the input/output controller 2084. The ROM 2010 stores a boot program performed when the computer 1900 starts up, and/or a program relying on the hardware of the computer 1900, and the like. The flexible disk drive 2050 is configured to read out a program or data from the flexible disk 2090, and provide it to the hard disk drive 2040 via the RAM 2020. The input/output chip 2070 connects the flexible disk drive 2050 to the input/output controller 2084, and connects various types of input/output devices to the input/output controller 2084, for example, via a parallel port, a serial port, a keyboard port, a mouse port, or the like.

The program provided to the hard disk drive 2040 via the RAM 2020 is stored in a recording medium, such as the flexible disk 2090, the CD-ROM 2095, or an IC card, and provided by a user. The program is read out from the recording medium, installed on the hard disk drive 2040 in the computer 1900 via the RAM 2020, and executed in the CPU 2000.

A program installed in the computer 1900 and causing the computer 1900 to function as the arithmetic device 170 includes an imaging device control module, a detection module, an association module, and an analysis module. These program or modules may work on the CPU 2000 or the like to cause the computer 1900 to function as the imaging device control unit 171, the recording unit 190, the identification unit 350, the detection unit 400, the association unit 550, and the analysis unit 600, respectively.

The information processing described in these programs is read by the computer 1900 to cause the computer to function as the imaging device control unit 171, the recording unit 190, the identification unit 350, the detection unit 400, the association unit 550, or the analysis unit 600 which is a specific means realized by cooperation of software and the various types of hardware resources described above. These specific means implement operations or processing of information corresponding to the intended use of the computer 1900 in the present embodiment, and the arithmetic device 170 is thereby constructed to be specific for the intended use.

As an example, when communication is performed between the computer 1900 and an external device or the like, the CPU 2000 is configured to execute the communication program loaded on the RAM 2020, and provide the communication interface 2030 with communication processing instructions on the basis of the content of the process written in the communication program. In response to the control by the CPU 2000, the communication interface 2030 is configured to read out the transmission data stored in the transmission buffer region or the like provided on the storage device, such as the RAM 2020, the hard disk drive 2040, the flexible disk 2090, the CD-ROM 2095, or the like, and transmit this transmission data to the network, and write reception data received from the network onto a reception buffer region or the like provided on the storage device. In this way, the communication interface 2030 may transfer transmission/reception data to the storage device through DMA (Direct Memory Access) scheme, and alternatively, the CPU 2000 may transfer the transmission/reception data by reading the data from the storage device or communication interface 2030 that are the origins of transfer, and writing the data onto the communication interface 2030 or the storage device that are the destinations of transfer.

In addition, the CPU 2000 causes all or necessary portions of files or database stored in an external storage device such as the hard disk drive 2040, the CD-ROM drive 2060 (CD-ROM 2095), and the flexible disk drive 2050 (flexible disk 2090) to be read into the RAM 2020 by means of DMA transfer or the like, and then performs various types of processing on the data in the RAM 2020. The CPU 2000 writes back the data on which processing is completed into an external storage device by DMA transfer or the like. In such processing, the RAM 2020 can be regarded as carrying contents of the external storage device temporarily, and thus the RAM 2020, the external storage device and the like are collectively called a memory, a recording unit, a storage device or the like in the present embodiment.

Herein, the storage device or the like stores information necessary for information processing of the arithmetic device 170, for example, moving image data or the like as necessary, and supplies the information to each component of the arithmetic device 170 as necessary.

Various types of information such as various types of programs, data, tables, databases or the like in the present embodiment according to the present embodiment are stored on such a storage device, and are subjected to information processing. Note that, the CPU 2000 can retain a part of the RAM 2020 in a cache memory and read from or write to the cache memory. In such a configuration as well, the cache memory serves a part of the function of the RAM 2020, and therefore the cache memory is also included with the RAM

2020, the memory, and/or the storage device in the present embodiment, except when it is shown with distinction.

In addition, the CPU 2000 is configured to execute various types of processing including various types of computations, information processing, conditional determination, information search/replacement, or the like described in the present embodiment for the data read from the RAM 2020, as specified by the instruction sequence of the program, and writes the result back onto the RAM 2020. For example, when performing conditional determination, the CPU 2000 compares various types of variables shown in the present embodiment to determine whether they satisfy conditions such as being larger than, smaller than, equal to or greater than, less than or equal to, equal to or like other variables or constants, and if a condition is satisfied (or if it is not satisfied) branches to a different instruction sequence or calls up a subroutine.

In addition, the CPU 2000 can search for information stored in a file in the storage device or the database, or the like. For example, if a plurality of entries, each having an attribute value of a second attribute associated with an attribute value of a first attribute, are stored in a storage device, the CPU 2000 searches, from among the plurality of entries stored in the storage device, an entry having an attribute value of the first attribute that matches a specified condition, and reads out the attribute value of the second attribute stored in the entry, and it is thereby possible to obtain the attribute value of the second attribute associated with the first attribute that satisfies a predetermined condition.

The programs or modules shown above may also be stored in an external recording medium. As a recording medium, other than the flexible disk 2090 and the CD-ROM 2095, an optical recording medium such as DVD or CD, a magneto-optical recording medium such as MO, a tape medium, a semiconductor memory, such as IC card, or the like can be used. Also, a storage device such as a hard disk or RAM that is provided with a server system connected to the Internet or a specialized communication network may be used as the recording medium to provide the programs to the computer 1900 via the network.

In the present disclosure, a configuration in which the arithmetic device 170 includes the CPU 2000 as a processor has been described, but the type of the processor is not particularly limited. For example, a GPU, an ASIA, an FPGA, or the like can be appropriately used as the processor. In addition, in the present disclosure, a configuration in which the arithmetic device 170 includes the hard disk drive 2040 as an auxiliary storage device has been described, but the type of the auxiliary storage device is not particularly limited. For example, instead of the hard disk drive 2040 or in addition to the hard disk drive 2040, another storage device such as a solid state drive may be used.

While the present invention has been described by way of the embodiments, the technical scope of the present invention is not limited to the above described embodiments. It is apparent to persons skilled in the art that various alterations or improvements can be made to the above described embodiments. It is also apparent from the scope of the claims that the embodiments added with such alterations or improvements can be included in the technical scope of the invention.

The operations, procedures, steps, and stages of each process performed by a device, system, program, and method shown in the claims, embodiments, or diagrams can be performed in arbitrary order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

EXPLANATION OF REFERENCES

1: device for analyzing neurons;
7: optical fiber;
10: imaging device;
culture dish;
23: stage;
27: objective lens portion;
34: fluorescent filter portion;
38: imaging lens portion;
40: transmitted illumination unit;
41: collector lens;
44: field lens;
45: polarized mirror;
47: light source for transmitted illumination;
50: timeline;
52: stop button;
53: fast-rewind button;
54: playback button;
55: fast-forward button;
60: slider bar;
70: light source for excitation;
100: chamber;
103: display region;
104: display region;
105: playback controlling portion;
107: display region;
108: display region;
109: display region;
150: microscope unit;
160: output unit;
170: arithmetic device;
171: imaging device control unit;
180: input unit;
190: recording unit;
300: camera;
350: identification unit;
400: detection unit;
411: field lens;
452: polarized mirror;
550: association unit;
600: analysis unit;
1900: computer;
2000: CPU;
2010: ROM;
2020: RAM;
2030: communication interface;
2040: hard disk drive;
2050: flexible disk drive;
2060: CD-ROM drive;
2070: input/output chip;
2075: graphics controller;
2080: display device;
2082: host controller;
2084: input/output controller;
2090: flexible disk; and
2095: CD-ROM.

What is claimed is:
1. A method of analyzing neurons, comprising:
acquiring an image by acquiring time-series images obtained by imaging a neuron in time series;

identifying a cell region by identifying a region of a neurite or a region of a cell body of the neuron on a basis of the time-series images;

detecting aggregates by detecting, on a basis of the time-series images obtained by imaging, in time series, first fluorescent protein tagged to specific protein expressed in the neuron, presence or absence of aggregates of the specific protein aggregated in the region of the neurite or the region of the cell body identified in the identifying the cell region by using, as a basis, luminance of the first fluorescent protein included in the time-series images; and performing an analysis by classifying the neuron into a plurality of groups on a basis of a detection result of the detecting the aggregates and analyzing a survival state of the neuron for each of the groups, wherein the survival state of the neuron includes at least any one of a survival period of time or a survival rate of the neuron, and the performing the analysis includes displaying, for each of the groups, a relationship between the plurality of groups and survival states of the plurality of groups.

2. The method of analyzing neurons according to claim 1, wherein the time-series images have at least one of data of a phase difference image, data of a fluorescence image including the luminance of the first fluorescent protein, or data including a moving image file.

3. The method of analyzing neurons according to claim 2, wherein the identifying the cell region includes imaging, in time series, the first fluorescent protein tagged to the specific protein expressed in the neuron in the acquiring the image, and identifying, as the region of the neurite of the neuron, a region where the luminance of the first fluorescent protein in the time-series images exceeds a first luminance threshold.

4. The method of analyzing neurons according to claim 3, wherein in the identifying the cell region, a region exceeding a predetermined size threshold among regions including the region where the luminance of the first fluorescent protein in the time-series images exceeds the first luminance threshold is identified as the region of the neurite or the cell body of the neuron, and further, each of the neurite being identified and identical and the cell body being identified and identical is tracked in time series, and a survival period of time related to the survival state is calculated.

5. The method of analyzing neurons according to claim 3, wherein the detecting the aggregates includes detecting the region of the neurite identified in the identifying the cell region as a region where the aggregates of the specific protein exist, and recognizing, as one aggregate region, a plurality of the aggregates in which a distance between regions where the aggregates exist is closer than a distance threshold in the time-series images.

6. The method of analyzing neurons according to claim 3, wherein in the identifying the cell region, a region where the luminance of the first fluorescent protein in the time-series images exceeds a second luminance threshold different from the first luminance threshold is identified as the region of the cell body of the neuron, and in the detecting the aggregates, the presence or absence of the aggregates of the specific protein is detected on a basis of comparison between the luminance of the first fluorescent protein and the first luminance threshold, in the region of the cell body identified in the identifying the cell region.

7. The method of analyzing neurons according to claim 1, wherein in the identifying the cell region, the region of the cell body or the neurite of the neuron is further identified on a basis of the time-series images obtained by imaging, in time series, second fluorescent protein expressed in the neuron and different from the first fluorescent protein, in the detecting the aggregates, whether the aggregates in the neurite identified exist in an axon or whether the aggregates exist in a dendrite is detected on a basis of the first fluorescent protein and the second fluorescent protein, and in the performing the analysis, on a basis of a detection result of the detecting the aggregates, the neuron is classified into a cell group in which the aggregates in the neurite exist on a side close to the cell body and a cell group in which the aggregates exist on a side close to a terminal of the neurite, and the survival state of the neuron is analyzed for each of the cell groups.

8. The method of analyzing neurons according to claim 7, further comprising performing association by specifying association between the cell body and the neurite constituting the neuron on a basis of the time-series images of the first fluorescent protein or the second fluorescent protein, wherein the performing the analysis includes classifying the neuron into a plurality of cell groups on a basis of the detection result of the presence or absence of the aggregates in the neurite and the presence or absence of the aggregates in the cell body in the detecting the aggregates with respect to the cell body and the neurite associated in the performing the association, and analyzing the survival state of the neuron for each of the cell groups.

9. The method of analyzing neurons according to claim 3, wherein the performing the analysis includes determining, on a basis of the luminance of the first fluorescent protein included in the time-series images, that the neuron is dead if luminance of the neurite or the cell body of the neuron is less than the first luminance threshold or less than a second luminance threshold, and calculating, as a survival period of time of the neuron, a period of time until the luminance of the neurite or the cell body is in a state of less than the first luminance threshold or less than the second luminance threshold, and displaying, on a display unit, a relationship between the detection result of the presence or absence of the aggregates in the neurite and the presence or absence of the aggregates in the cell body detected in the detecting the aggregates and the survival period of time of the neuron.

10. A device for analyzing neurons, comprising:

an imaging device that comprises a microscope and a camera and that acquires time-series images obtained by imaging a neuron in time series; and a processor programmed to:

identify a region of a neurite or a region of a cell body of the neuron on a basis of the time-series images;

detect, on a basis of the time-series images obtained by imaging, in time series, first fluorescent protein tagged to specific protein expressed in the neuron, presence or absence of aggregates of the specific protein aggregated in the identified region of the neurite or the region of the cell body of the neuron by using, as a basis, luminance of the first fluorescent protein included in the time-series images; and classify the neuron into a plurality of groups on a basis of a result of the detection and analyze a survival state of the neuron for each of the groups, wherein the survival state of the neuron includes at least any one of a survival period of time or a survival rate of the neuron, and the processor is further programmed to cause to be displayed, for each of the groups, a relationship between the plurality of groups and survival states of the plurality of groups.

11. The device for analyzing neurons according to claim 10, wherein the processor is further programmed to image, in time series, the first fluorescent protein tagged to the specific protein expressed in the neuron in the imaging device, and identify, as the region of the neurite of the neuron, a region where the luminance of the first fluorescent protein in the time-series images exceeds a first luminance threshold.

12. The device for analyzing neurons according to claim 11, wherein the processor is further programmed to identify, as the region of the neurite or the cell body of the neuron, a region exceeding a predetermined size threshold among regions including the region where the luminance of the first fluorescent protein in the time-series images exceeds the first luminance threshold, and further track, in time series, each of the neurite being identified and identical and the cell body being identified and identical, and calculate a survival period of time related to the survival state.

13. The device for analyzing neurons according to claim 11, wherein the processor is further programmed to detect the identified region of the neurite as a region where the aggregates of the specific protein exist, and recognize, as one aggregate region, a plurality of the aggregates in which a distance between regions where the aggregates exist is closer than a distance threshold in the time-series images.

14. The device for analyzing neurons according to claim 11, wherein the processor is further programmed to identify, as the region of the cell body of the neuron, a region where the luminance of the first fluorescent protein in the time-series images exceeds a second luminance threshold different from the first luminance threshold, and detect, in the region of the cell body identified, the presence or absence of the aggregates of the specific protein on a basis of comparison between the luminance of the first fluorescent protein and the first luminance threshold.

15. A non-transitory computer-readable storage medium, which has stored thereon a computer program, having therein instructions that, when executed by a processor or a programmable circuit, cause the processor or the programmable circuit to perform operations comprising the method of analyzing neurons according to claim 1.

* * * * *